US012579718B1

(12) United States Patent
Holt

(10) Patent No.: US 12,579,718 B1
(45) Date of Patent: Mar. 17, 2026

(54) HANDLING TRUNCATED DATA IN ITERATIVE RECONSTRUCTION

(71) Applicant: Varex Imaging Corporation, Salt Lake City, UT (US)

(72) Inventor: Kevin Holt, Chicago, IL (US)

(73) Assignee: Varex Imaging Corporation, Salt Lake City, UT (US)

( * ) Notice: Subject to any disclaimer, the term of this patent is extended or adjusted under 35 U.S.C. 154(b) by 255 days.

(21) Appl. No.: 17/013,648

(22) Filed: Sep. 6, 2020

Related U.S. Application Data

(60) Provisional application No. 62/896,978, filed on Sep. 6, 2019.

(51) Int. Cl.

| | |
|---|---|
| ***G06T 11/00*** | (2006.01) |
| ***G06T 17/20*** | (2006.01) |
| ***G16H 30/40*** | (2018.01) |
| ***G16H 50/20*** | (2018.01) |
| ***G16H 50/70*** | (2018.01) |

(52) U.S. Cl.
CPC .......... *G06T 11/008* (2013.01); *G06T 17/205* (2013.01); *G16H 30/40* (2018.01); *G16H 50/20* (2018.01); *G16H 50/70* (2018.01); *G06T 2210/41* (2013.01); *G06T 2211/424* (2013.01)

(58) Field of Classification Search
CPC .... G06T 11/003; G06T 11/006; G06T 11/008; G06T 2207/20201; G06T 2207/30004; G06T 2207/10072; G06T 2207/10081; G06T 2210/41; G06T 2211/424; G06T 2211/432
See application file for complete search history.

(56) References Cited

U.S. PATENT DOCUMENTS

2011/0103662 A1* 5/2011 Chiang .................... A61B 6/03 382/130
2012/0141006 A1* 6/2012 Koehler ................ G06T 11/006 382/131
2012/0308099 A1* 12/2012 Benson ................ G06T 11/006 382/131
2013/0328919 A1* 12/2013 Holt ....................... G01N 23/04 345/629
2019/0076101 A1* 3/2019 Pan ........................ A61B 6/032
(Continued)

OTHER PUBLICATIONS

Tian et al., "GPU-based Low Dose CT Reconstruction via Edge-preserving Total Variation Regularization", Aug. 2011, IOP Publishing, Physics in Medicine and Biology 56(18):5949-67, p. 1-21 (Year: 2011).*
(Continued)

*Primary Examiner* — Vincent Rudolph
*Assistant Examiner* — Timothy Choi
(74) *Attorney, Agent, or Firm* — Dorsey & Whitney LLP

(57) ABSTRACT

Technology is described for handling truncated data in iterative reconstruction. A method comprises iterating on a volume of an object including a non-truncated part based on image data and at least one truncated part representing deficiently imaged data. The volume is represented by voxels. The iterating includes regularizing the non-truncated part of the volume using a first regularizer, and regularizing the truncated part of the volume using a second regularizer different from the first regularizer.

19 Claims, 10 Drawing Sheets

(56) References Cited

U.S. PATENT DOCUMENTS

2020/0105032 A1* 4/2020 Yang .......................... G06T 5/70
2021/0012543 A1* 1/2021 Hein ..................... G06T 11/008

OTHER PUBLICATIONS

Dang et al., "Multi-resolution statistical image reconstruction for mitigation of truncation effects: application to cone-beam CT of the head", Dec. 29, 2016, Institute of Physics and Engineering in Medicine, Physics in Medicine & Biology, vol. 62, p. 539-559. (Year: 2016).*
Schmitt et al., "Fast Variance Prediction for Iteratively Reconstructed CT Images With Locally Quadratic Regularization", Jan. 2017, IEEE, IEEE Transactions on Medical Imaging. vol. 36, No. 1, p. 17-26. (Year: 2017).*
Fessler et al., "Spatial Resolution Properties of Penalized-Likelihood Image Reconstruction: Space-Invariant Tomographs", Sep. 1996, IEEE Transactions on Image Processing, vol. 5, No. 9., p. 1346-1358. (Year: 1996).*
R. Azencott et al, "Searchlight CT: A new reconstruction method for collimated X-ray tomography", Proceedings of the 5th International ICST Conference on Performance Evaluation Methodologies and Tools, 2011.
Hansis et al, Iterative Reconstruction for Circular Cone-Beam CT with an Offset Flat-Panel Detector, IEEE Nuclear Science Symposuim & Medical Imaging Conference, 2010.
Danielsson et al. Toward exact 3D-reconstruction for helical cone-beam scanning of long objects. Proc. 3D' 97 Conf., Nemacolin, PA, pp. 141-144. 1997.
Feldkamp et al. Practical cone-beam algorithm. J. Opt. Soc. Am. A./vol. 1, No. 6, Jun. 1984. p. 612-619.
Lionheart. What is sufficient data for stable CT reconstruction? Presentation at School of Mathematics, Univ. of Manchester, Nov. 4, 2013.
Proska et al. The n-PI-Method for Helical Cone-Beam CT. IEEE Transactions on Medical Imaging, vol. 19, No. 9, Sep. 2000. pp. 848-863.
Smith. Cone-beam Tomography: Recent Advances and a Tutorial Review. Optical Engineering 1990; 29: 5: 524-534.
Smith. Image Reconstruction from Cone-Beam Projections: Necessary and Sufficient Conditions and Reconstruction Methods. IEEE Transactions on Medical Imaging, vol. MI-4, No. 1, Mar. 1985. 14-25.
Tam et al. Exact cone beam CT with a spiral scan. Phys. Med. Biol., vol. 43, pp. 1015-1024, 1998. Abstract provided.
Tang et al. On the data acquisition, image reconstruction, cone beam artifacts, and their suppression in axial MDCT and CBCT—A review. Med. Phys. 45 (9), Sep. 2018. e761-e782.
Tuy. An Inversion Formula for Cone-Beam Reconstruction. SIAM Journal on Applied Mathematics, Jun. 1983, vol. 43, No. 3, pp. 546-552.

* cited by examiner

HANDLING TRUNCATED DATA IN ITERATIVE RECONSTRUCTION

BACKGROUND

Unless otherwise indicated herein, the approaches described in this section are not prior art to the claims in this disclosure and are not admitted to be prior art by inclusion in this section. In computed tomography (CT), an image is reconstructed from projections of an object. The desired scan field of view (FOV) to be imaged may be smaller than entire object scanned, such as the mouth relative to the entire head, the heart relative to the rest of the abdomen, or a tumor relative to the rest of the body. Iterative reconstruction (IR) of the image based on the projections of the object can be facilitated by a series of consecutive estimations, guesses, or other mathematical updates that optionally include statistical, physics-based, model-based, or other a-priori knowledge of the object and/or imaging apparatus. Some challenges with reconstruction can occur when the complete scan FOV is truncated relative to the scanned object, which can violate typical data sufficiency conditions (DSC) required for proper reconstruction.

DETAILED DESCRIPTION OF SOME EXAMPLE EMBODIMENTS

Figure 1:
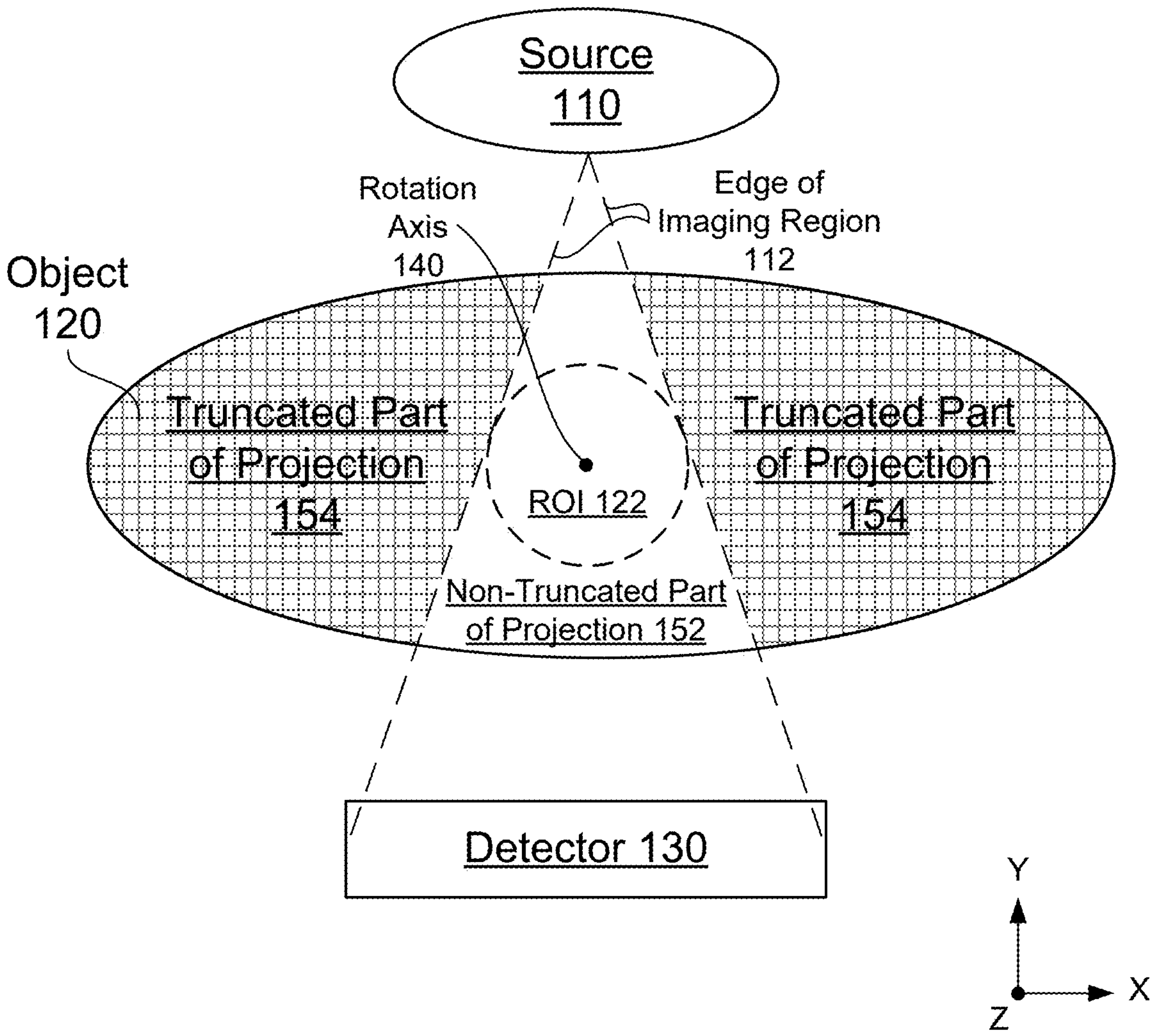
FIG. 1 illustrates a schematic or block diagram of an x-ray source, an object, a detector, and a truncated and non-truncated part of projection.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Numbers provided in flow charts and processes are provided for clarity in illustrating steps and operations and do not necessarily indicate a particular order or sequence. Unless otherwise defined, the term "or" can refer to a choice of alternatives (e.g., a disjunction operator, or an exclusive or) or a combination of the alternatives (e.g., a conjunction operator, and/or, a logical or, or a Boolean OR).

Disclosed embodiments relate generally to mechanisms, methods, and systems to address truncation issues in iterative reconstruction (IR). Disclosed embodiments also relate generally to a type of statistical reconstruction, targeted reconstruction, and/or zoomed reconstruction.

Some challenges with reconstruction can occur when the complete scan field of view (FOV) is truncated relative to the scan of the object. Examples of truncated scan field of views can occur in the following: In dental scans, centering the scan field of view on the mouth, and not taking complete data on the rest of the head. For cardiac scans, centering the scan field of view on the heart, and not taking complete data on the rest of the abdomen. For oncology, centering the scan field of view on a tumor, and not taking complete data on the rest of the body. For oncology or other medical scans where the couch shows up in some of the views but not all of them. For industrial scans, centering the scan field of view on some suspect location for possible defects, and not taking complete data of the rest of the part.

One challenge is that if real-world material is visible in any of the projections, then some reconstruction algorithms require that material is or needs be reconstructed in the three-dimensional (3D or 3-D) volume, even if that portion of the object is not interesting to the user or to the basic imaging task or the focus of the image—often referred to as the "truncation issue". Different algorithms can tolerate the truncation issue to different extents. Some algorithms, such as so-called "local tomography" are designed to exactly reconstruct truncated data to within some unknown additive constant. Most filtered-backprojection algorithms are somewhat tolerant of truncation, where truncation may result in a mild artifact, but the artifact can generally be mitigated by ad-hoc corrections such as a smooth extrapolation of projection-image borders before a filtering step. Filtered-backprojection is an especially popular class of reconstruction algorithms, and most notably includes FDK (cone-beam algorithm of Feldkamp, Davis, and Kress—a widely used filtered back projection [or back projection] algorithm for 3D CBCT reconstruction found in L.A. Feldkamp et al, "Practical cone-beam algorithm", J. Opt. Soc. Am. A 1, 612-619, 1984, which is incorporated by reference in its entirety).

Iterative reconstruction (IR) techniques are especially susceptible to truncation artifacts that can be difficult to mitigate. Iterative reconstruction refers to iterative algorithms used to reconstruct images (typically two-dimensional (2D or 2-D) or 3D images) using certain imaging techniques, and generally feature iteratively improving a guess or estimate (or set of guesses or estimates) for the reconstruction until an acceptable image is found. For example, in computed tomography (CT), such as cone beam computed tomography (CBCT), an image is reconstructed from projections of an object. CBCT is an imaging technique consisting of x-ray computed tomography where the x-rays are divergent in two dimensions, forming a cone (or pyramid) shaped beam. In CT, iterative reconstruction (IR) techniques often produce higher quality images, though at a higher computational cost, than common filtered back-projection (FBP) methods. Whereas FBP directly calculates the image in a single reconstruction step but typically involves a number of somewhat unrealistic assumptions about the object, the acquisition, and the physics, IR techniques take multiple passes to generate an image but can employ much more realistic assumptions about the object, the acquisition, and the physics, and can be extended to leverage various forms of a priori knowledge. Iterative reconstruction techniques each typically starts with an assumed image (e.g., many viable approaches can be used to supply this initial guess, such as all zeroes, some constant value, a shape such as a water cylinder, or even a first-pass FBP reconstruction), computes projections from the image, compares the original projection data and updates the image based upon the difference (or generalized difference, such as a ratio) between the calculated and the actual projections. Forward-projected data is compared with the actual measured data according to statistical metrics and the computed difference is used in conjunction with a back-projection operator and additional updates to create a new updated image with either lower noise, better fidelity to the measured data, and/or better consistency with the a priori knowledge. This sequence is repeated until some stopping criteria is reached, such as a maximum number of iterations is reached, the cost function stops appreciably improving, or the difference between actual measured data and the new forward-projected data becomes acceptably low.

In contrast, filtered back projection uses an analytic inverse of the Radon transform (or a fan-or cone-beam variation of the Radon transform), where the analytic inverse consists primarily of a ramp filter followed by backprojection. A ramp filter is a filter whose frequency response varies linearly with frequency (though in practice this filter may be modified by some additional apodization—an optical filtering technique for changing the shape of a function, signal, transmission, or structure). Back-projection for cone-beam CT refers to tracing the 2D projections over the 3D volume, possibly also incorporating a weighting such as $1/R^2$ weighting, and adding the 2D projection's pixel (i.e., dexel) values onto the 3D volume's voxel values. Similarly, back-projection for fan-beam CT refers to tracing the one-dimensional (1D or 1-D) projections over the 2D reconstruction. Filtered backprojection refers to the combination of a ramp filter, followed by back-projection, with some additional weightings in order to make a 2D (for fan-beam) or 3D (for cone-beam) reconstructed image. For an idealized continuous detector taking images over a continuous trajectory (with infinitely fine dexels and infinitely many images with infinitely fine angular spacing) for fan-beam imaging filtered-backprojection is the theoretical inverse of the Radon transform, which models CT acquisition for an ideal pencil beam with no noise or with uniform gaussian noise. In practice, the method can also be discretized and applied on real 1D or 2D projection data, which can violate some of the theoretical assumptions of the algorithm but can still give useful images, albeit sometimes with artifacts.

Various approaches to iterative reconstruction applied to CT include algebraic reconstruction or the Algebraic Reconstruction Technique (ART), Simultaneous Algebraic Reconstruction Technique (SART), Simultaneous Iterative Reconstruction Technique (SIRT), Separable Paraboloidal Surrogates (SPS), Penalized Weighted Least Squares (PWLS), Prior Image Constrained Compressed Sensing (PICCS), iterative Sparse Asymptotic Minimum Variance (iSAMV) algorithm (iterative, parameter-free super-resolution tomographic reconstruction method inspired by compressed sensing), statistical reconstruction (SR), Model-Based Iterative Reconstruction (MBIR), and learned iterative reconstruction (e.g., updating an algorithm learned from training data using techniques from machine learning such as convolutional neural networks, while still incorporating the image formation model).

Statistical iterative image reconstruction algorithms typically comprise five components: (1) an object model that expresses the unknown continuous-space function that is to be reconstructed in terms of a finite set of values with unknown coefficients that must be estimated from the data; (2) a system model that relates the unknown object to the "ideal" measurements that would be recorded in the absence of measurement noise; (3) a statistical model that describes how the noisy measurements vary around the ideal values, typically assuming either Poisson or Gaussian noise; (4) a cost function that is to be minimized to estimate the image values (often represented unwrapped as one long vector), where often the cost function includes some form of regularization; and (5) an algorithm, usually iterative, for minimizing the cost function, including some initial estimate of the image and some stopping criterion for terminating the iterations. A cost function or a loss function is a function that maps an event or values of one or more variables onto a real number intuitively representing some "cost" associated with the values or events. An optimization problem seeks to minimize the cost function (or loss function). The regularization term of (4) can often be thought of as a sixth major component, and the regularization term can represent prior knowledge about the scan object (which can lead to reduced noise or improved image quality), and/or better condition the cost function to improve numerical stability. Regularization is a common technique used in mathematics, statistics, finance, computer science, image processing, machine learning, and inverse problems (such as CT), and in general is the process of adding information in order to solve an ill-posed problem or to prevent overfitting. In CT reconstruction, regularization typically involves penalizing images that are unrealistic (e.g., images that have lots of noise or physically impossible values such as negative density). One particularly common approach for CT regularization is to penalize the gradient of an image (using e.g., Tikhonov, Huber, pseudo-Huber, or TV regularization) which has the effect of smoothing the image. Often edge-preserving regularizers are chosen for smoothing the image, which have the effect of edge-preserving smoothing.

Figure 2:
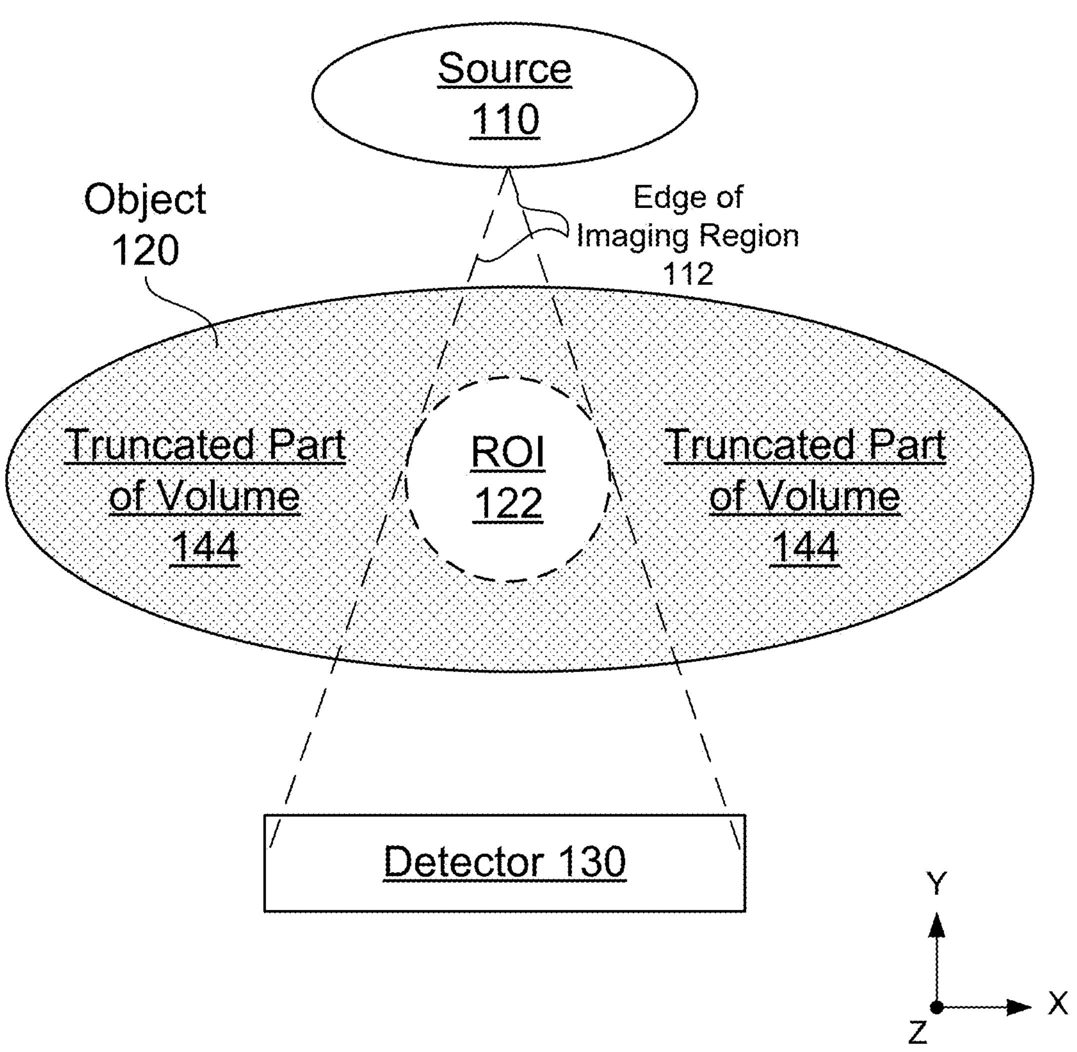
FIG. 2 illustrates a schematic or block diagram of an x-ray source, a region of interest (ROI) and truncated part of volume on an object, and a detector.

FIGS. 1 and 2 illustrate an x-ray imaging source 110 and a detector 130 are used to image an object 120. Features in the figures are for illustration and are not drawn to scale or may not represent the realistic spacing or arrangement between the features. For example, in FIGS. 1-2 the x-ray imaging source 110 and a detector 130 are shown as closer and smaller than the object 120. In FIG. 1, the x-ray imaging source 110 has a beam with an edge of imaging region 112 defining an edge of an image captured by the detector 130. In this example, the source 110 and detector 130 rotate in a circle around the rotation axis 140, and their rotational position is known as a projection angle. For any given projection angle, the beam crosses part of the object so that the detector images some non-truncated part of the projection 152, but does not image a corresponding truncated part of the projection 154. As the source 110 and detector 130 rotate, the truncated 154 and non-truncated 152 regions of the projection change accordingly. By intersecting the non-truncated projection regions 152 for every projection angle, this process traces out a circle 122 that is in the non-truncated projection region 152 for every view angle.

As shown in FIG. 2, the rest of the object 120 is in the projection truncation region 154 for at least some projection angles. Therefore, for certain algorithms such as Full-fan (or FullFan) reconstruction (which is one of the most direct version of FBP or FDK), region 122 is referred to as the non-truncated part of the volume, and 144 is referred to as the truncated part of the volume. Note that volume truncation and projection truncation are therefore related but different. Most commonly in truncated imaging, the goal of imaging is only to reconstruct the non-truncated region 122, also referred to as the reconstruction region of interest (ROI) 122. ROI 122 might also be referred to as the "scan field of view", which is another notation for the field of view that has complete coverage without truncation. Although not shown in FIG. 2, the rotation axis 140 of FIG. 1 also exists in the center of the ROI 122.

One solution to reconstruct projections with truncation is to just reconstruct the large volume, including the extraneous material or region 144, then crop out the extraneous material or region 144 later to discard the unwanted data. However, some of that extraneous material may not be well captured in the projection data, and therefore may be reconstructed poorly, which may then also adversely affect the reconstruction of the region of interest.

Figure 3:
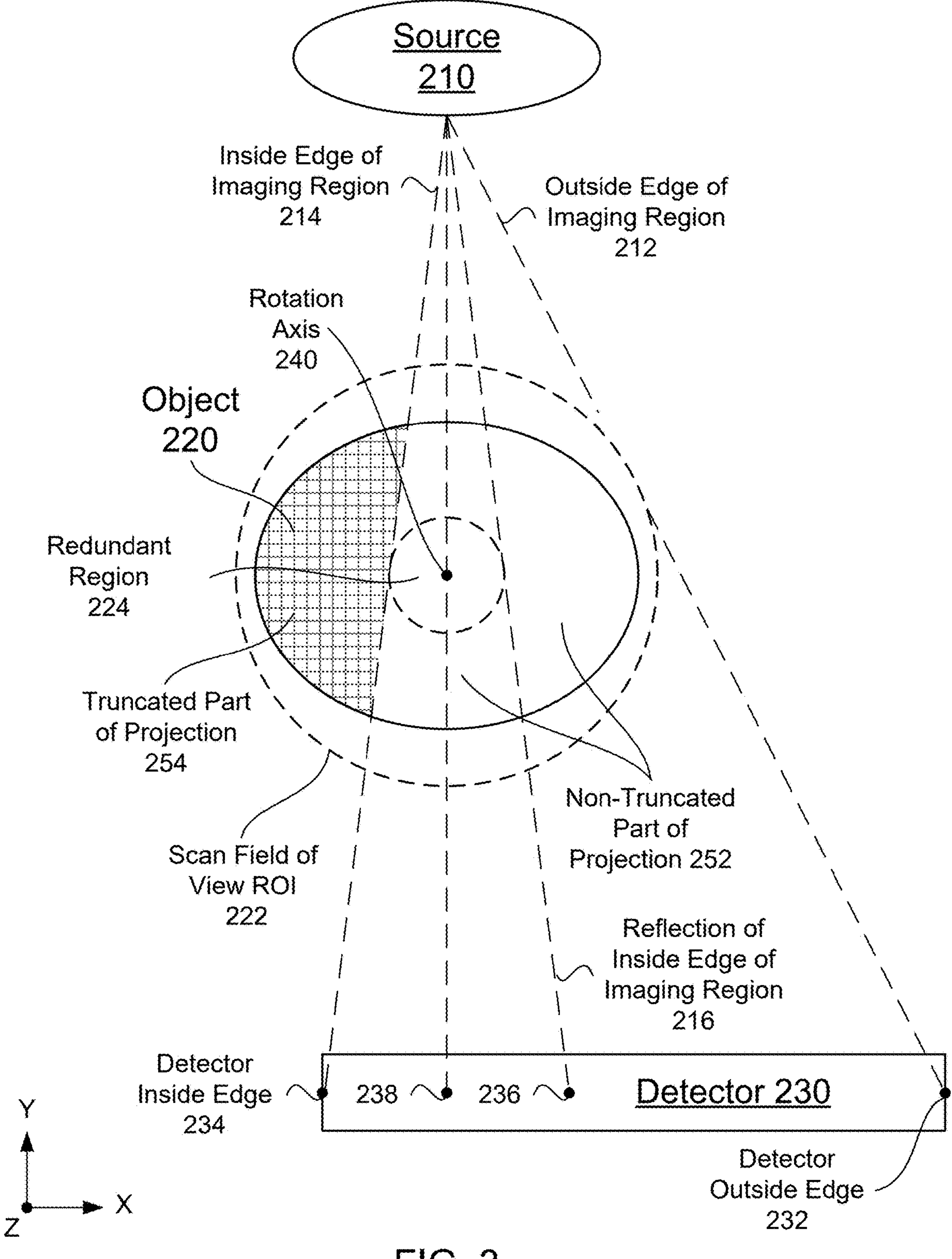
FIG. 3 illustrates a schematic or block diagram of an x-ray source, an object, a detector, and a truncated and non-truncated part of half-fan projection.
Figure 4:
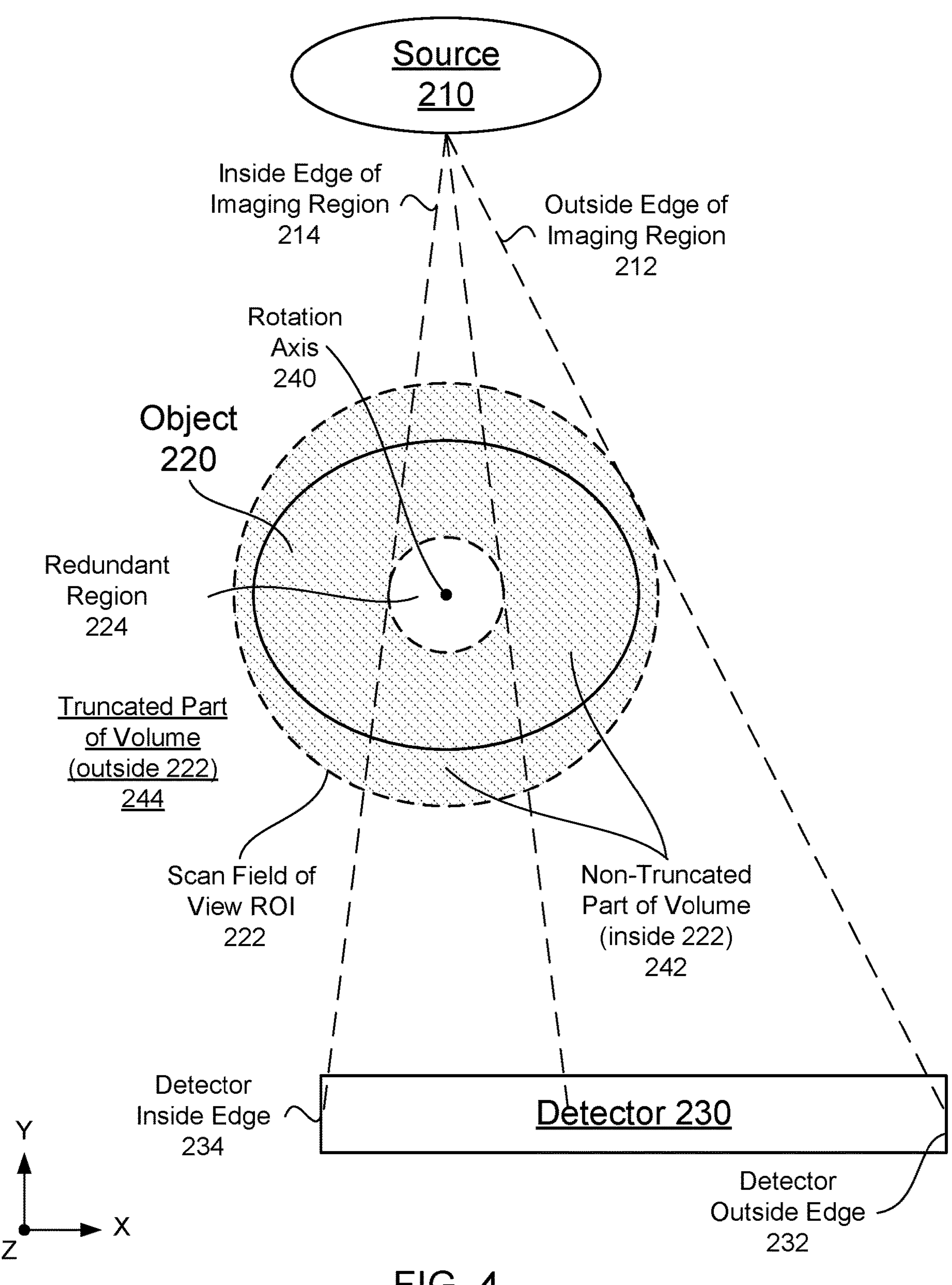
FIG. 4 illustrates a schematic or block diagram of an x-ray source, a scan field of view region of interest (ROI) on an object, and a detector.

Additionally, some individual projection frames may appear cropped, whether or not the entire object is truncated relative to the entire scan field of view. For example: Half-fan (or HalfFan, also sometimes referred to as asymmetric or offset scanning) data is cropped on one side, where the edge 234 of the detector 230 falls within the scan object (vertically from the x-ray imaging source 210). FIGS. 3 and 4 illustrate an x-ray imaging source 210 and detector 230 are used to image an object 220 where only one detector edge 234 falls inside the object while the other detector edge 232 falls outside the object. Some of the object 220 is seen by the detector 230 and is called the non-truncated part of the projection 252, while some of the object is not seen by the detector and is called the truncated part of the projection 254. In this example, the source and detector rotate 360 degrees in a circle about the rotation axis 240, and as they rotate the truncated 254 and non-truncated 252 parts of the projection change accordingly. Then regions 254 and 252 combined produce three different regions.

A first region or the redundant region 224 contains the portion of the object that is in the non-truncated part 252 of every projection, similar to the ROI 122 in FIGS. 1 and 2. Each point in 224 is considered redundantly imaged because for every projection image redundant data exists in the projections roughly 180° around the object where the object is imaged from the opposite direction. Imaged beam edge 214 represents the inside edge of the imaging region about the rotation axis 240 on the opposite of the outside edge of the image region 212, and is also tangential to the redundant region 224. Line 216 represents the reflection of the inside edge of the imaging region about the rotation axis 240 within the outside edge of the image region 212, and is also tangential to the redundant region 224. The inside edge 234 of the detector, the outside edge 232 of the detector, the projection 238 of the rotation center 240, and the projection 236 of reflected inside edge 216 mark different points on the detector 230. The edge of the redundant region in the detector is defined by inside edge 234 and the projection 236 of reflected inside edge 216, which defines the redundant region in the volume 224.

Whereas some reconstruction algorithms require an object to be visible in 360° worth of acquisition, so-called Half-Fan algorithms only require the object to be visible in a smaller range of acquisition, typically around 180° plus (+) the fan angle. For such algorithms, the scan field of view ROI 222 is limited by the outside detector edge 212, and defines the boundary between the truncated part of the volume 244 and the non-truncated part (also referred to as the HalfFan non-truncated part) of the volume 242. The second region or the non-truncated region of the volume 242 is the region where the object is in the non-truncated region of a projection for at least 180° worth of projection angles. In general, for some algorithms (such as HalfFan FDK), the non-truncated region 242 has enough data to reconstruct the volume. In consideration of these algorithms, the non-truncated region 242 (and not just the redundant region 224) is considered to be a HalfFan reconstruction region. Most commonly, in half-fan imaging, the goal of imaging is to reconstruct the HalfFan non-truncated region 242. A third region or truncated region 244 represents the truncated part of the volume that even a HalfFan algorithm cannot reconstruct—this presents the same reconstruction challenges as the truncated part of the volume 144 in FIG. 2.

Many objects are truncated axially, for example long-aspect-ratio objects such as a human torso, an arm or a leg, a tree, or a rocket motor. Axially truncated objects may be truncated along one axis or direction but not along the other axes or directions. For example, an object might be truncated along Z axis but not in X and Y axes (where Z is perpendicular to FIGS. 1-4, coming out of the page or into the page).

For some reconstruction algorithms, such as half-fan FDK, the data is typically pre-weighted using half-fan weighting prior to reconstruction, but that approach is generally incompatible with statistical reconstruction (since artificially lowering the dexel values makes the dexels appear to have lower transmission or equivalently more object material, and hence can make extraneous material show up in the interior of a reconstructed volume, especially in the ROI 222). A dexel is a physical point or smallest addressable element (usually in 2D space) in an imaging detector represented in an image as a value, where a voxel represents a value on a regular grid in 3D space, such as in a reconstructed volume. A dexel ("detector element") refers to the analog of a pixel ("picture element") but more specifically refers to pixels in the projection data (or data captured by the detector) as opposed to voxels in the reconstructed volume.

In addition, some pre-processing corrections may be less accurate near the detector borders 232 and/or 234. For example, 2D deconvolution approaches such as fast adaptive scatter kernel superposition (fASKS) (for scatter correction) or Varex Imaging Corporation's proprietary Resolution Enhancement Algorithm (REA) (for detector deblur) can't see past the edge of the detector, and thus 2D deconvolution approaches can't be expected to perform as well near the border of the projection images relative to the interior of the projection images. Half-fan pre-weighting can de-emphasize any such border regions that may have poorer correction quality (so in addition to performing half-fan reconstruction, as a side-effect half-fan weighting can also help mitigate additional artifacts), but since iterative reconstruction may not use standard half-fan pre-weighting, the border data in iterative reconstruction does not generally get the de-emphasis that half-fan weighting gives. As such, for half-fan imaging, iterative reconstruction may end up with mild artifacts, such as artifacts in the shape of a circle at the edge of the redundant region 224. An artifact is any error in the perception or representation of any information, introduced by the involved equipment, algorithm, or technique. Many well-known artifacts often occur in CT, including rings, streaks, banding, blurring, cupping, and shading.

Furthermore, detector borders 232 and/or 234 may introduce inconsistency problems, for example, if a slight uncorrected gradient occurs in the air signal, then complementary rays may be slightly inconsistent. These inconsistency issues can potentially lead to a discrete artifact where the reconstruction support abruptly changes from two rays (where there is redundant complementary data from 180 degrees apart) to one ray (where there is no redundant data). Again, half-fan weighting might conventionally de-emphasize these issues, where iterative reconstruction gets no such natural de-emphasis and can have an artifact in the shape of a circle right where the redundant region ends 224.

Extra Truncation Regularization-Border Feathering-Iterative Reconstruction (ETR-BF-IR)

In an example of iterative reconstruction, an Extra Truncation Regularization Iterative Reconstruction (ETR-IR) method and a Border Feathering Iterative Reconstruction (BF-IR) method are described as follows, as well as an ETR-BF-IR method which is the combination of the ETR-IR and BF-IR methods.

ETR-IR is iterating on a volume that is larger than the ROI 102 and 222. In one approach (or full object approach) the volume is large enough to hold all the object 120 and 220 (e.g., memory to hold the entire object), including both non-truncated parts 122 and 242 and truncated parts 144 and 244. A second approach (or extended ROI approach) is to make the volume substantially larger than the ROI 102 and 222 (e.g., when the first approach (or full object approach) requires too much memory or too much computation time), but perhaps still smaller than the full object 120 and 220. In either approach, when the iterations are finished, the resulting volume can be cropped down to just the ROI 102 and 222. In another example, cropping the volume can occur after de-weighting the data in the iterations and the iterations are completed. Thus, the projection data is not cropped, but only the volume data is cropped. Note that the forward-projection step of IR also selects how to handle volume borders. In the first approach (or full object approach), the "zero" border mode (where all data outside the volume is assumed to be zero-valued) can accurately represent the volume outside the object 120 and 220. In the second approach (or extended ROI approach), in some cases, one or more directions may be extrapolated, for example for an axially truncated object that is roughly constant in Z (for example a human torso or a rocket motor), a volume that is smaller in Z than the full object may be reasonable to reconstruct using an extrapolation method such as nearest neighbor in the Z direction.

Conventionally, a forward-projection operator is a substep in an iterative reconstruction method, which can introduce some challenges. The iterations adjust the volume so that the total attenuation calculated by forward-projection matches the total attenuation measured by the detector. But if the detector senses some material that forward-projection doesn't get to "see," then forward-projection will underestimate the attenuation. Then the algorithm will determine that the forward-projection and measured data are different and the algorithm may end up putting extraneous material into the volume to compensate for the discrepancy, and ultimately lead to an artifact in the volume.

In the ETR-IR method, two different volume smoothing regularizers may be specified: (1) a normal regularizer (or standard regularizer or first regularizer) for the non-truncated region (and voxels) toward the inside of the image, and (2) a more aggressive regularizer for the truncated region (and voxels) toward the outside of the image. The second regularizer (or aggressive regularizer) encourages the reconstruction to be very smooth in the poorly-captured truncated region. Since the truncation region will eventually be discarded anyway, smoothing this region much more than normal, more than the normal regularizer, is acceptable. A regularizer provides regularization, which modifies the cost function, and its effect is typically controlled using a regularization weight value. Regularization has several advantages. First, regularization adds numerical stability. Some unregularized methods, such as ART, may not necessarily converge to a global minimum, whereas regularized methods are generally more likely to converge stably. In many cases, the stronger the regularization (i.e., the higher the regularization weight), the better defined is the global optimum and hence the more stable is the convergence. Second, regularization allows noise reduction, where different regularizers (such as quadratic, total variation (TV), Huber, or wavelet methods) may enforce different noise shapes in the reconstructed image, and where more regularization leads to more the noise reduction. Some regularizers, in particular TV or Huber regularization, are also specifically designed to preserve larger edges while smoothing out more subtle features that are more likely to be noise. Third, regularization allows one to include a priori information in the imaging task. Whereas unregularized reconstruction can often be thought of as maximum-likelihood (ML) estimation, regularized reconstruction can often be thought of as maximum a posterior (MAP) estimation, which can be similar to ML with an additional term to represent the a priori distribution of the expected object to be reconstructed. For example, the prior distribution might reflect that the reconstructed image should have small gradients, or be piecewise smooth. Often the regularizer is derived for one of the three reasons above, but can then be reinterpreted in another. For example, quadratic regularization is equivalent to assuming some Gaussian distribution for the gradient of the reconstructed image, and Total Variation (TV) regularization is equivalent to assuming a Laplacian distribution of the image gradient.

The aggressive regularizer can be determined by regularization weight and/or edge preserving characteristics (or lack thereof) relative to the normal regularizer. A higher weight is more aggressive, lesser weight is less aggressive. An edge is the boundary of a feature in an image, and some regularizers give special treatment to edges in a reconstructed volume image. Edge-specific techniques such as edge enhancement and edge preservation are well known in image processing and computer vision. With regard to ETR-IR, edge-preserving regularization can be considered less aggressive than non-edge-preserving regularization. An edge preserving method (like TV or Huber) used in an edge preserving regularizer will smooth out small edges (e.g., noise) but try to preserve large edges (e.g., real image features, such as the interface between bone and tissue). A small edge is an image feature on volume edge with a small corresponding gray level change, and a large edge is an image feature on volume edge with a large corresponding gray level change. Edge preservation does not preserve all actual image feature and exclude all noise on the volume edge, and in general some noise in edge preserving methods might look like large edges and get preserved, while some real but subtle textures may get smoothed out as noise. However, in many cases edge preserving methods tend to generate cleaner reconstructions than non-edge preserving methods for non-truncated data. Using a non-edge preserving regularizer (like Quadratic) is more aggressive since the regularizer tries to smooth out all edges regardless of whether the edges are large or small (i.e., false large edges can survive edge-preserving regularization but not nonedge-preserving regularization). Additionally, some edge-preserving regularizers (like Huber, but not TV) have a threshold parameter for deciding how large should an edge be in order to preserve that edge. Raising the threshold parameter is more aggressive since a higher threshold parameter preserves fewer edges in the image.

Then, the ETR-IR method specifies a "content-penalty" for the truncated region, which weights, forces, or, encourages all voxel values to be zero-valued (or close to zero valued or near zero valued) toward the edge of the volume, where very little information resides and where iterative reconstruction algorithm is less stable. Whereas conventional regularization techniques penalize some measure of the gradient (e.g., Expressions 1 and 2), the content penalty penalizes the values themselves (e.g., Expression 3), where u is the reconstructed volume, and R is the regularizer value.

$$\text{Quadratic Gradient: } R_Q(\mu)=\Sigma_{x,y,z}|\nabla\mu_{x,y,z}|^2 \quad \text{[Expression 1]}$$

$$TV\text{: } R_{TV}(\mu)=\Sigma_{x,y,z}|\nabla\mu_{x,y,z}| \quad \text{[Expression 2]}$$

$$\text{Quadratic Content: } R_C(\mu)=\Sigma_{x,y,z}(\mu_{x,y,z})^2 \quad \text{[Expression 3]}$$

$R_Q$ and $R_{TV}$ are smallest when the gradient of the image $\nabla\mu$ is small, or equivalently when the image $\mu$ is smooth. But $R_C$ is smallest when u itself is small, which encourages u towards being zero valued. If $R_C$ were applied to all voxels, $R_C$ would encourage all voxel values to be zero, but the ETR-IR method only sums over the voxels in the truncated region, which encourages truncated values to have smaller values but does not affect non-truncated voxels. In an example, spatial regularization or a spatial regularizer refers to regularization that penalize some measure of the gradient (e.g., Expressions 1 and 2). In an example, content penalty regularization, a content penalty regularizer, or content penalty module refers to regularization where the content penalty penalizes the values themselves (e.g., Expression 3).

Note that iterative reconstruction also includes a fidelity term that is minimized when the forward-projection's calculated projection data are consistent with the measured data (also taking the statistical model into account), but this term is generally (and intentionally) at odds with minimizing the regularizer. Therefore, the reconstructed image is some compromise or combination between minimizing fidelity and minimizing the regularization term(s), where the tradeoff is controlled by regularization weights. Specifically ETR-IR includes a tradeoff between (1) the fidelity term, (2) the conventional spatial regularizer in the non-truncated region, (3) the aggressive spatial regularizer in the truncated region, and (4) the content penalty in the truncated region, and iteratively searches for the best compromise between these four constraints. Typically this tradeoff is implemented with Lagrange multipliers, leading to a cost function J(μ) represented by Expression 4.

$$J(\mu)=F(\mu)+\lambda_N R_N(\mu)+\lambda_T R_T(\mu)+\lambda_C R_C(\mu) \quad \text{[Expression 4]}$$

F is the fidelity term, $R_N$ is the non-truncated regularizer (e.g., TV or Huber regularization), $R_T$ is the truncated regularizer (e.g., quadratic regularization), $R_C$ is the content penalty, $\lambda_N$ is the non-truncated regularization weight, $\lambda_T$ the truncated regularization weight, and $\lambda_C$ is the content penalty regularization weight. By one approach the $\lambda_N$, $\lambda_T$, and $\lambda_C$ weights are determined empirically during system design. Alternatively, additional methods are known in the art for automatically determining regularizer weights for conventional IR, and such methods could potentially be adapted for use in the ETR-IR approach. The fidelity term/ measures the discrepancy between the reconstructed volume and the measured data. In general a minimum value of the fidelity term occurs when the forward projection of the estimated volume exactly matches the measured data. However, due to the ill-conditioned nature of forward projection, many theoretical reconstructed volumes may match the measured data and minimize the fidelity term even though most of those volumes are not physically realistic. And furthermore due to noise in the measured data, likely none of the generated solutions for the reconstructed volumes will actually be correct, and minimizing fidelity by itself may lead to an image with artifacts. Thus, including regularization terms are commonly added in the cost function, especially with noisy or incomplete data.

The BF-IR method smoothly de-weights the dexels (or equivalently weighting the dexels with small weights or weight less than one) near the edge of the detector. In an example, smoothly de-weighting the dexels changes the weights at a continuous decrement, such as a regular decrement like −0.1 decrement resulting in 1.0, 0.99, 0.98, 0.97, . . . weights or gradual increasing decrement value like 1.0, 0.99, 0.975, 0.95, 0.92, . . . weights. An example of non-smoothly (or abrupt) de-weighting the dexels changes the decrement abruptly (discontinuously) between weights, such as 1.0, 0.99, 0.98, 0.9, 0.1, 0.02, 0.01, 0.0. Iterative reconstruction searches for a volume whose forward-projection is consistent with the measured data. This consistency with the measured data is measured by the fidelity term and is calculated as a function of dexel values, and the fidelity term can be modified to give some dexels less weight than others. The BF-IR method gives border dexels less weight, using a smooth feathering function that goes smoothly to zero at the image border. Feathering is a technique used in computer graphics to smooth or blur the edges of a feature. BF-IR can be parameterized in several ways. In the "fixed-border" (FB) method, a fixed border size is configured, either in units of dexels, or in units of physical distance (e.g., millimeters [mm]). BF-IR then feathers the dexels corresponding to the specified fixed border size along each image border. The border sizes can be configured differently for each of the top, bottom, left, and right borders of the detector. For half-fan data, setting up fixed-border feathering at the inside edge 234 can mitigate abrupt transitions and associated artifacts at the edge of the redundant region 224.

For half-fan data, BF-IR also supports a "redundancy weighting" (RW) method, that can provide weighting with some similarities to traditional half-fan weighting. As an example, referring to FIG. 3, the weight function with weight coefficient is 1.0 from the outside edge of the detector 232 to the edge of the redundant region 236. In the redundant region, the weight function starts at 1.0 at the edge of the redundant region 236, then decreases halfway to 0.5 at the projection of the rotation center 238, then all the way to zero at the inside edge of the detector 234. In another example, a different weight function with weight coefficients can be used between the outside edge of the detector 232 and the edge of the redundant region 236, between the edge of the redundant region 236 and the projection of the rotation center 238, and between the projection of the rotation center 238 and the inside edge of the detector 234 using decreasing values or decrement. The weight function can be a sigmoidal function (e.g., having a characteristic "S" "-shaped curve or sigmoid curve) as in traditional half-fan weighting, or the weight function can be a linear function. BF-IR can also combine the FB and RW methods. For example for the outside edge using the fixed-border method, and for the inside edge first shifting the inside edge 234 by the fixed border amount, and feathering based on that shifted point, and making the weight zero between the original and shifted versions of 234.

The stopping criterion for terminating the iterations can be a specified number or predetermined count of iterations (e.g., 20 iterations), stopping with a measurement on the cost function decreases below a specified value, or similar stopping criteria used in the disclosed methods.

Truncation, Reconstructable Region, and Data Sufficiency Conditions (DSC)

Conventionally for circular scans, different treatment may be given to "axial truncation" (in the Z direction) versus "in-plane truncation" (in the XY direction). But the BF-IR and ETR-IR methods can also address other trajectories such as helical, saddle, circle+line, tomosynthesis, or even completely arbitrary or unstructured trajectories.

The word "truncation" can apply to different features or objects, including projections and volumes in IR. "Truncation" applied to projections, such as a truncated projection, refers to some of the object that is not visible in the projection image. "Truncation" as applied to volumes, generally means some portion of the object that is not included the reconstruction volume. In general if some projection data is available for a volume, then the volume can be divided into an "exactly-reconstructable" region and a "not-exactly-reconstructable" region, where the "not-exactly-reconstructable" region can be further subdivided into an "approximately-reconstructable" region and a "severely deficient" region (or "unreconstructable" region). For circular scans, the reconstruction region is approximately cylindrical, where the central slice within the cylinder is exactly reconstructable, the rest of the cylinder is approximately reconstructable, and outside of the cylinder is severely deficient. For some trajectories (such as circle) there is a sharp dividing line between the approximately reconstructable region and the severely deficient region. In some trajectories the transition from approximately reconstructable to severely deficient can be gradual with no firm dividing line.

Academic research has investigated data sufficiency conditions (DSC) for deciding whether or not an object can be exactly reconstructed.

For example, published papers and presentations include: (1) H. Tuy, "An inversion formula for cone-beam reconstruction," SIAM Journal on Applied Mathematics 43, 546552, 1983; (2) Smith BD, "Image reconstruction from cone-beam projections: necessary and sufficient conditions and reconstruction methods," IEEE Trans Med Imaging, 1985; 4:14-25; (3) Smith BD, "Cone-beam tomography: recent advances and a tutorial review," Opt Eng 1990; 29:524-534; (4) Tang et al, "On the data acquisition, image reconstruction, cone beam artifacts, and their suppression in axial MDCT and CBCT," Med Phys 45 (9), September 2018; (5) Bill Lionheart, "What is sufficient data for stable CT reconstruction?" presentation on Nov. 4, 2013, (6) Proksa et al, "The n-PI-Method for Helical Cone-Beam CT," IEEE Trans Med Imaging, 2000 Sep. 19 (9): 858-63; (7) P. E. Danielsson, P. Edholm, J. Eriksson, and M. Magnusson-Seger, "Toward exact 3D-reconstruction for helical cone-beam scanning of long objects," in Proc. 3D'97 Conf., Nemacolin, PA, pp. 141-144; and (8) K. C. Tam, S. Samarasekera, and F. Sauer, "Exact cone beam CT with a spiral scan," Phys. Med. Biol., vol. 43, pp. 1015-1024, 1998, which are incorporated by reference in their entirety.

For non-truncated projections (or an infinitely large detector), Tuy and Smith came to similar conclusions, which are generally known as the Tuy conditions (or Tuy-Smith conditions). The criterion is based on source trajectory (i.e., the locus of points in space that the x-ray source passes through as the CT scan is performed. Tuy's condition can be stated as: "If every plane that intersects the object intersects the source trajectory, then one has complete information about the object" or equivalently "If every plane that intersects the object contains a source-spot location, then one has complete information about the object." If this Tuy condition is satisfied so that one has complete information about the object, then the object can be exactly reconstructed. The mathematical statement/expression is independent of the actual choice of reconstruction algorithm, and places bounds on what any plausible reconstruction algorithm can do-outside these bounds, reconstruction is theoretically impossible.

Figures 5, 6A:
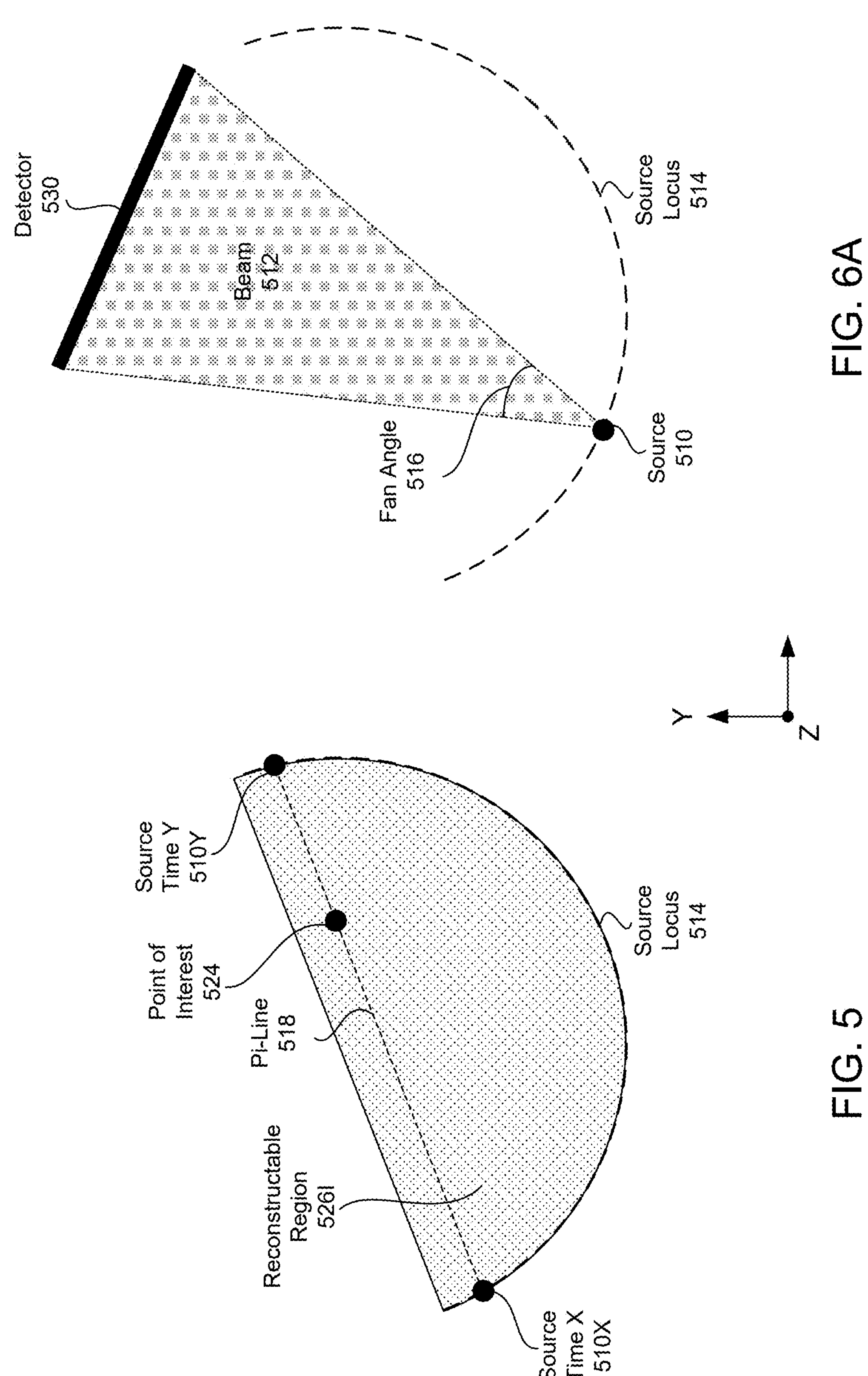
FIG. 5 illustrates a schematic or block diagram of a reconstructable region from conventional pi-line on a source locus of an infinite detector model.
FIG. 6A illustrates a schematic or block diagram of a finite detector setup.

A related concept is pi-lines (as discussed by Tam and Danielsson references), as illustrated by FIG. 5. The classical definition of a pi-line again assumes an infinite detector (or infinite sized detector, where in both directions the span of the source beam projection angle 516 generating projection data and its accompanying detector is 180° or near 180° shown in FIG. 6A), and is as follows: For any point of interest (POI) 524 in the volume, if there is a line segment that passes through that POI and also intersects the scan trajectory at both ends (510X and 510Y), then that line segment is considered a classical pi-line (conventional pi-line) 518 for that point. The source locus 514 is path that a source 510 travels in time to generate various projections of the object. A source spot location 510X represents the source 510 at time X and a source spot location 510Y represents the source 510 at time Y, and additional data (not illustrated) is also taken when the source is at points on the locus between times X and Y. In theory if any point is on a pi-line then complete information about that point is available and that point can be exactly reconstructed. This statement about the pi-line was originally derived for helical reconstruction (see Tam and Danielsson references), but has since been extended to other trajectories such as saddle reconstruction, and may hold for any trajectory. A reconstructable region 526I of the infinite detector model (where "I" represents infinite) is illustrated in FIG. 5.

Figures 6B, 6C:
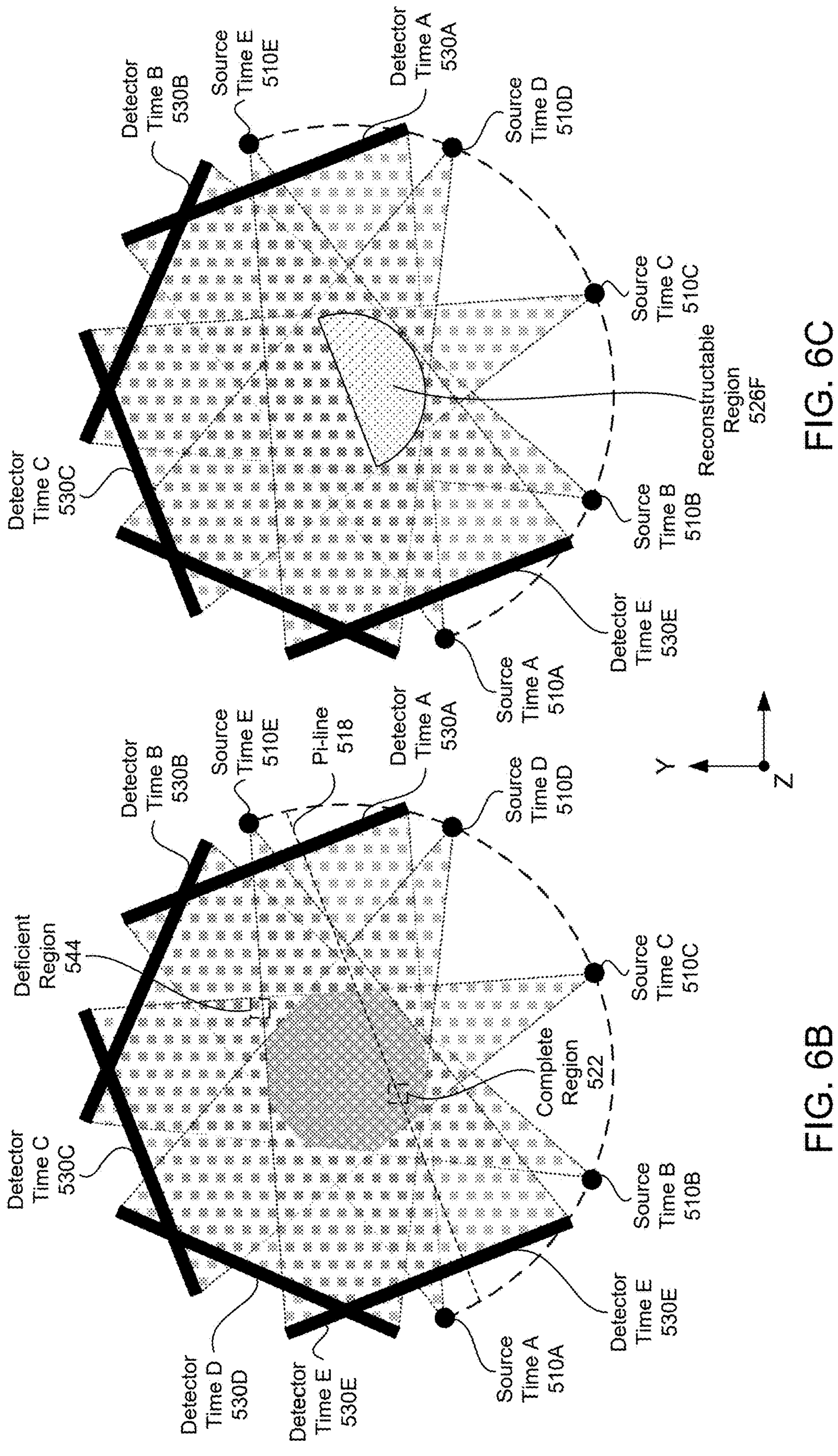
FIG. 6B illustrates a schematic or block diagram of projected regions, a complete region, and a deficient region in a finite detector model.
FIG. 6C illustrates a schematic or block diagram of a reconstructable region from hybrid pi-line on a source locus of a finite detector model.

One limitation with the classic Tuy condition and classic pi-lines is that these models do not allow for finite detector 530 (with a finite size). FIGS. 6A-6C illustrate projected regions (e.g., projection beam 512), a complete region 522, a deficient region 544, and a reconstructable region 526F in a finite detector model and setup (where "F" represents finite). However, the concept of pi-lines can be extended to finite detectors, so definition of pi-line is modified as follows: For any POI in the volume, a line segment is only a pi-line 518 if (as with the classical pi-line definition) the line segment passes through that point and also intersects the scan trajectory at both ends, and for each source spot location 510A-E on the source spot locus 514 connecting the two ends of the pi-line, the ray from the source spot through the POI must intersect the interior of the detector 530A-E. The source spot locations 510A-E represents the source 510 at times A-E, and detector locations 530A-E represents the detectors 530 at times A-E. With this modified (finite detector) view of the pi-line definition and with a suitable algorithm, reconstructing any point that has a pi-line should be theoretically possible.

The shaded octagon in FIG. 6B is the part of the volume that is present in every projection. In other words, if an arc was long enough to cover 180° plus the fan angle then the whole shaded octagon would be reconstructable (like 526F)

but for a shorter arc (e.g., A through E) then the part of the octagon that is outside 526F is deficient.

One challenge with DSC's is what happens when the condition is not satisfied and complete information about a point does not exist. In general, if there is not complete information about a point, then no algorithm can stably and exactly recover that point. However, some algorithms may still be able to get close to a correct value. In general, incomplete information can generally be thought of in two main categories: almost-complete information (in an approximately-reconstructable region), and severely deficient information (in a severely deficient region).

For circular scans, the entire source trajectory is located within the central slice, and so every point in the central slice 526F satisfies Tuy's condition, and therefore the central slice can be recovered exactly (assuming at least the projections aren't truncated). However, for non-zero cone angles (of the projection in the Z direction on FIG. 6A), a plane exists that is parallel to the central plane that does not intersect the central slice, and so the slice cannot be reconstructed (at least not stably and exactly). Therefore, for circular scans, convention reconstruction algorithms cannot exactly and stably reconstruct any slice other than the central slice. Yet circular trajectories are still quite common and important, and while circular scans don't have fully complete information, circular scans still contain a lot of information, at least enough to get an approximate reconstruction. For example, the Radon transform (e.g., FIG. 4*a* in Tang 2018) of the acquired data can be inspected. For a circular scan, the Radon transform carves out a donut shape in Radon space where data exists with a hole in the middle where no data exists. This hole corresponds to a null-space where object information is lost and so cannot be exactly and stably recovered. But most of Radon space is properly captured and since the hole is typically a relatively small part of the data, the data with the small hole can be considered almost-complete data.

In contrast, the "truncated" regions 144 and 244 in FIGS. 2 and 4, pi-lines only exist for a small portion of Radon space (e.g., less than half), which are regions considered severely deficient. In severely deficient regions very little data is available to make even a useful approximate reconstruction.

When considering CT volumes, each volume point is considered to be "reconstructable" if the volume point is complete or almost-complete, and each volume point is considered to be "unreconstructable" if the volume point is severely deficient. For example, for a circular cone-beam full-fan 360 degree scan, the reconstructable region is a tapered-cylinder (whose central slice is complete and the rest of the volume is almost-complete), and everything outside that cylinder (in XY) and above or below that cylinder (in Z) is deficient and unreconstructable. For other trajectories, such as laminography or tomosynthesis, a blurrier line or distinction exists between almost-complete and deficient. The determination between almost-complete and deficient regions is based on the scanner, trajectory, algorithm, and imaging task.

As used herein, an imaging scanner or iterative reconstruction device has truncated projections if at least one of its projection images is truncated, regardless of the volume considerations. A scanner or iterative reconstruction device has a truncated acquisition (or volume acquisition) if at least some part of the object extends into the unreconstructable region. A scanner or iterative reconstruction device has a truncated volume FOV if at least some part of the object extends outside the reconstruction volume.

Searchlight CT Method or Azencott Approach

Other alternatives to handling truncated data in iterative reconstruction include the methods found in R. Azencott et al, "Searchlight CT: A new reconstruction method for collimated X-ray tomography", Proceedings of the 5th International ICST Conference on Performance Evaluation Methodologies and Tools, 2011, which is incorporated by reference in its entirety.

In the Azencott approach (or Searchlight CT paper or approach), the full-sized volume is reconstructed (i.e., the truncated ROI plus the outside truncation region) by: (1) Forward-projecting the volume, and (2) in the forward-projection, replacing the non-truncated part with the measured data, analogous to an extrapolation. The new projection images are the same as the measured data for the portion where measured data actually exists, and outside the projection the data is taken from the forward-projection.

Then the Azencott approach, (3) applies filtered back-projection to get an improved full-sized volume, and (4) for the truncated (outside) part of the image, regularizes the image by partitioning the truncated portion of the volume and in each truncation, replacing the voxel values with the local average, and (5) repeating steps 1-4.

The BF-IR and ETR-IR methods have a number of advantages over the Searchlight CT approach. First, the Searchlight CT approach or method always forces the forward-projected data to be exactly equal to the measured data. The ETR-IR method allows the two to be different, for example using a Poisson model, penalized-weighted-least-squares, standard least squares, and the like. A Poisson distribution describes probability of a given number of events occurring in a fixed interval of time and/or space if these events occur with a known constant rate and independently of the time since the last event, and in CT a Poisson model typically uses a Poisson distribution where the events are photon absorption events, the time interval is a detector integration window, the space interval is the dexel's active detection area, and the known constant rate is the expected photon flux calculated from the forward projected current volume estimate. Least squares is a standard approach in regression analysis to approximate the solution of overdetermined systems (i.e., sets of equations in which more equations exist than unknowns). Least squares means that the overall solution minimizes the sum of the squares of the residuals made in the results of every single equation. Least squares can also be derived by replacing a Poisson model with a Gaussian model with similar noise variance for every pixel. Weighted least squares can be considered an extension of standard least squares where each residual is scaled by some specified weighting, typically to account for the different noise levels in each residual. In CT, weighted least squares is often used to achieve a good compromise between the accuracy of Poisson weighting versus the computational advantages of Gaussian weighting by adjusting the weights of a Gaussian model to mimic the effect of a Poisson model.

As stated another way, the Searchlight CT method assumes that the measured projection data is noiseless, which is not physically realistic. The ETR-IR method allows for a realistic noise model.

Second, the Searchlight CT method does not regularize the region of interest, and hence does not perform any noise reduction. The ETR-IR method allows arbitrary regularization in the region of interest, which allows customizable noise reduction.

Third, the Searchlight CT method uses a crude regularizer that may destroy high-frequency information in the truncated region. Specifically, the Searchlight regularizer relies on replacing various sections of image data in various regions with the average pixel value over each region. In one approach, the ETR-IR method uses a quadratic regularizer in the truncated region. The quadratic regularizer avoids discontinuities in the truncated region (a potential disadvantage of the Searchlight regularizer), and allows the amount of regularization to be continually adjusted, to better preserve what useful information does actually exist in the truncated region (which useful information can be more easily destroyed by the Searchlight regularizer). This ETR-IR approach therefore allows a system designer or user to adjust the regularization to preserve as much or as little high-frequency information from the truncation region as is required for a specifid imaging task.

Inherently, iterative reconstructions have a risk of diverging, and for truncated scans that risk may be elevated in the truncated region since very little data may be available to work with or use in the model. Fourth, the Searchlight CT method requires a number of assumptions in order to assure convergence, including a sufficiently large ROI, and some specific mathematical concerns that may not necessarily be satisfied in practice. The constraint that a sufficiently large ROI is needed is especially challenging given that the one of the objectives of zoomed reconstruction is to facilitate smaller ROIs. For the ETR-IR method, a non-zero content penalty prevents the method from diverging in the truncated region, regardless of its size.

Fifth, the Searchlight CT method has no features to address real-world non-idealities, like imperfect corrections or inconsistencies in complementary rays.

The Searchlight CT method relies on filtered backprojection, which opens up a number of configuration questions in terms of sampling and filter choice. Furthermore the Searchlight CT method seems to assume that filtered backprojection actually inverts the forward-projection operation (where the forward-projection is referred to as the "x-ray transform"), which may not be accurate (and can introduce error in the model) as filtered backprojection generally assumes zero cone angle (which is an invalid assumption for CBCT), and infinitely fine sampling (which is an invalid assumption for pixel-based detectors), and an infinite framerate (which is not physically possible), so the Searchlight CT method is unlikely to handle non-ideal effects like large cone angle or discrete sampling. In contrast, the ETR-IR and BF-IR approaches more accurately models non-ideal effects (including large cone angle or discrete sampling), by avoiding filtered backprojection and instead solving a ray-tracing consistency problem instead. Ray tracing is a rendering technique for generating an image by tracing the path of light as pixels in an image plane and simulating the effects of its encounters with a virtual object.

Hansis Method

Another alternative to handling some of the issues with truncated data in iterative reconstruction include the methods (or Hansis method or Hansis approach) found in Hansis et al, Iterative Reconstruction for Circular Cone-Beam CT with an Offset Flat-Panel Detector, IEEE Nuclear Science Symposuim & Medical Imaging Conference, 2010 (referred to as the Hansis paper), which is incorporated by reference in its entirety.

In the Hansis method, axial truncation is addressed by: Extrapolating the projection data in the Z direction, then reconstructing onto a taller or longer volume (e.g., longer than the object).

The Hansis method addresses the half-fan issue of pre-weighted data using half-fan weighting by: Using a redundancy weighting function (where the weights for complementary rays sum to one, similar to the redundancy weighting function used for half-fan FDK). Stated another way or more simplistically, for each projection frame in the first 180° (a first projection frame): (1) Find a second complementary projection frame, 180° away, (2) forward-project both frames, (3) perform the typical iterative update calculations on the two forward-projected frames, and for each pixel in each of the two frames, calculate the correction value that should get backprojected onto the volume (but don't backproject yet), and (4) for each voxel, (a) ray-trace from the source through the voxel to find where it intersects the detector and repeat for both projection frames, and (b) take a weighted average of the two corresponding projection pixel values, and add that to the voxel value.

The BF-IR and ETR-IR methods have a number of advantages over the Hansis method:

First, the Hansis method only handles axial truncation and the half-fan issue, but does not address a fully truncated ROI. Stated another way, the Hansis method cannot handle truncation on all four detector edges at once.

For handling axial truncation, extrapolating projection data is imperfect and unreliable, especially when the object is not constant in Z. The Hansis method extrapolation approach may be acceptable or sufficient for a human torso, which is roughly cylindrical and extrapolating a little in Z can work somewhat as long as the torso is aligned to the rotation axis. But for non-cylindrical objects such as a human head, human or animal extremities, or industrial parts, the extrapolation may not work well. In contrast, the ETR-IR method enforces that the volume is consistent with the measured projection data, but only for the measured data (or imaged data) that actually exists. The ETR-IR method has no consistency constraints between the volume and non-existent dexels. Thus, the ETR-IR method leads to reconstructions where the volume only matches the actual measured data, while the volume in the Hansis method can match made-up extrapolated data that may not necessarily be very accurate.

Second, in FDK, projection pixel weights are required to sum to one for complementary rays, otherwise shading errors result. The Hansis approach asserts that projection pixel weights are required to sum to one for complementary rays for iterative reconstruction, but the Hanis summing constraint is not actually or theoretically necessary in iterative reconstruction. Experimental demonstrations have shown that if there are no inconsistency issues or border issues then half-fan reconstructions can be successfully performed with no redundancy weighting whatsoever. The Hansis paper claims that an artifact will occur if redundancy weighting is not performed, but some of the figures/images (e.g., FIG. 4) in the Hansis paper shows streaks that appears to be more like an artifact from imperfect borders. The Hansis paper even refer to the streaks as a "discontinuity" artifact. So, second, the Hansis paper adds a redundancy weighting scheme into iterative reconstruction that is unnecessary and may actually degrade image quality since some data is discarded that might otherwise still be usable. Another or better approach is to de-weight poorly corrected borders, and to soften discontinuities at the edge of the truncation region. The BF-IR method can de-weight poorly corrected edge or border pixel in the image representation without the expense, inflexibility, or degradation that are all inherent in using a redundancy weighting scheme that is not technically necessary.

Third, the Hansis method redundancy weighting scheme does not properly model photon statistics. If two x-rays have N photons, then the weighted average behaves as if N photons travelled through the voxel. However, a total of 2*N photons actually went through the voxel. The BF-IR redundancy-weighting method has a similar limitation. However, the BF-IR fixed-border method is able to better exploit the actual photon statistics, since the total weights (i.e., the combined weight from redundant rays 180° apart) are not constrained to add to one (1.0). The total weights in the BF-IR fixed-border method can be in a range from 0 to 2. Looking at the volume, the border of the redundant region 260 has total weight 1.0 but ramps up to total weight 2.0 at a distance inside the redundant region controlled by the fixed border size, and everything further inside the redundant region has total weight 2.0. So for full-fan scans, large overlap half-fan scans, or small borders, most of the redundant region has total weight 2.0. Outside the redundant region, the total weight is 1.0 up until a fixed-border's distance away from the non-truncation boundary, at which point it ramps down to 0.0 at the boundary of the non-truncated region. The BF-IR method accurately models the true available photon counts in the regions except for the small fixed border regions just inside the redundancy region boundary and just inside the non-truncated region boundary.

Fourth, the Hansis method is likely to be significantly slower than the BF-IR method. The BF-IR method uses a standard backprojector, which loops over each voxel to ray-trace it back to find the corresponding detector pixel value. This inner loop in ray tracing is one of the main bottlenecks of iterative reconstruction. Furthermore, the cache to those detector values is usually one of the limiting factors of backprojection and therefore of iterative reconstruction. The Hansis method doubles the demand on the inner loop, where their inner backprojection loop must ray-trace two different detector frames and pull information from each of the frames. The result is that for each voxel the Hansis method can only cache half as many projection values per frame, which can result in lower performance.

Fifth, the BF-IR method is parameterized in the domain of the actual problem (of finite detector imaging). By setting the border width parameter, the user can control how much to roll off imperfect borders, and how much to smooth discontinuities at the edge of the truncation region. The Hansis method has a weighting function whose width is controlled by the amount of detector offset, which often has no real relationship to the extent of the border issues or inconsistency issues. Whereas the Hansis method redundancy weighting is fixed and its width cannot be tuned without physically changing the scanner geometry, the BF-IR fixed-border method exposes a border width parameter for each detector edge, and those parameters can be freely adjusted during system design to be large enough to address potential border issues or inconsistency issues but not so large as to discard useful data.

The BF-IR and ETF-BF-IR methods provides a statistical reconstruction (SR) algorithm that offers an improved tradeoff of resolution, noise, and dose. Truncation occurs frequently in CBCT, which historically has been challenging to address in SR (and for iterative reconstruction generally). The BF-IR and ETF-BF-IR methods used in SR provides more accurate modeling by lowering the noise, which improves image quality, relative to FDK or non-statistical based IR for a similar resolution and dose. If the noise is tolerated or set to level similar to the FDK or non-statistical based IR, then BF-IR and ETF-BF-IR methods used in SR allows a user to lower the dose and/or reduce (or turn down) the regularization resulting in a higher resolution image.

Figure 7:
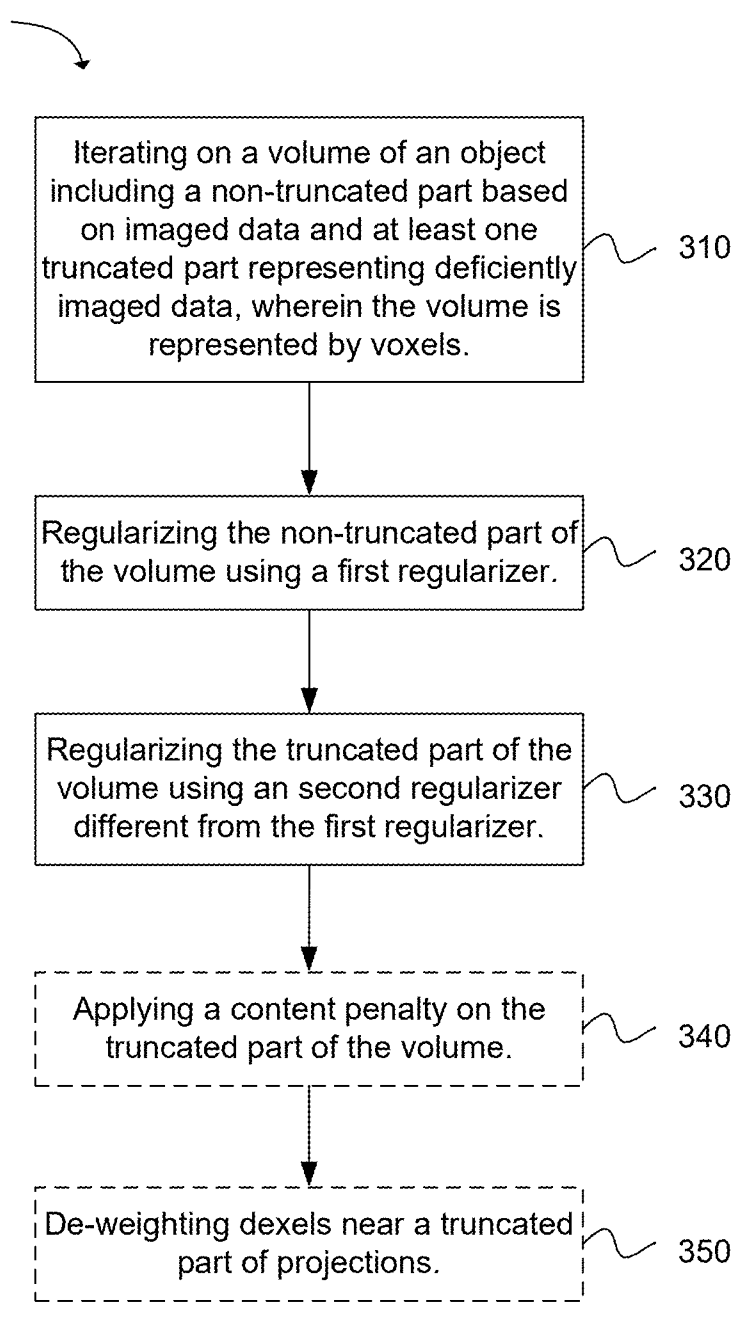
FIG. 7 is a flowchart illustrating an example of a method for handling truncated data in iterative reconstruction.

FIG. 7 illustrates a flowchart of a method for handling truncated data in iterative reconstruction 300. The method for handling truncated data in iterative reconstruction 300 comprises: iterating on a volume of an object 120 or 220 including a non-truncated part 122 or 242 based on imaged data and at least one truncated part 144 or 244 representing deficiently imaged data, wherein the volume is represented by voxels, as in step 310. As used herein, imaged data includes sufficiently imaged data or redundantly imaged data. As used herein, deficiently imaged data includes non-imaged data or deficiently imaged data. The iterating includes: regularizing the non-truncated part of the volume 122 or 242 using a first regularizer (or non-truncated regularizer) 422, as in step 320; and regularizing the truncated part of the volume 144 or 244 using a second regularizer (or truncated regularizer) 424 different from the first regularizer 422, as in step 330.

In some embodiments, iterating on the volume of the object 120 or 220 further comprises: applying a content penalty ($R_C$) on the truncated part of the volume 144 or 244, as in step 340.

In some embodiments, iterating on the volume of the object 120 or 220 further comprises: de-weighting dexels near a truncated part of projections 154 or 254, as in step 350. De-weighting refers to weighting values (e.g., dexels) with a weight that is less than one (<1.0). In an example, "dexels near" refers to within 5, 10, 25, 50, 100, 200, 300, or 400 dexels. In an example, de-weighting image data uses continuous decrement on dexels approaching the edge 232 and 234 of the detector 130 or 230. In another example, de-weighting image data de-weights a fixed border (FB) of dexels on at least one edge 232 and 234 of the detector 130 or 230 or includes reduced redundancy weighting (RW) for a redundancy region 122 or 224 of the detector 130 or 230.

In some embodiments, the non-truncated part of the volume is an unreconstructable part of the object 120 or 220. In an example, the second regularizer 424 is more aggressive than the first regularizer 422. In another example, the second regularizer 424 includes higher weight than the first regularizer (or normal regularizer) 422, or the second regularizer 424 includes a non-edge preserving regularizer and the first regularizer (or normal regularizer) 422 includes an edge preserving regularizer. In an example, the second regularizer 424 includes a content penalty regularizer with a content penalty whose value is lower for dexel values closer to zero, and higher for dexel values farther from zero (as described in relation to Expression 3).

In some embodiments, the first regularizer 422 comprises spatial regularization. In an example, the spatial regularization of the first regularizer 422 includes quadratic regularization, Huber regularization, pseudo-Huber regularization, TV regularization, or wavelet regularization. In some embodiments, the second regularizer 424 comprises spatial regularization. In an example, the spatial regularization of the second regularizer 424 includes spatial regularization comprises quadratic regularization, Huber regularization, pseudo-Huber regularization, TV regularization, or wavelet regularization. In an example, second regularizer comprises a spatial regularizer and a content penalty.

In some embodiments, regularizing the non-truncated part of the volume and regularizing the truncated part of the volume, further comprises: minimizing a sum of a fidelity term (F) and regularization terms, wherein the regularization terms include a first regularization term ($R_N$) corresponding to the first regularizer 422, a second regularization term ($R_T$) corresponding to spatial portion of the second regularizer 424, and a third regularization term ($R_C$) corresponding to a content penalty in the second regularization term ($R_T$) (or a third regularization term ($R_C$) corresponding to a content penalty of the second regularizer 424).

In some embodiments, iterating on the volume of the object 120 or 220, further comprises: storing the volume in memory 430 with a size to store the entire object 120 or 220.

In some embodiments, iterating on the volume of the object 120 or 220, further comprises: storing the volume in memory 430 with a size to store a portion of the object 120 or 220 with a dimension (or diameter) that is at least twice a dimension (or diameter) of a region of interest (ROI) 122 or 222 of the volume. In some embodiments, iterating on the volume of the object 120 or 220, further comprises: storing the volume in memory 430 with a size to store a portion of the object 120 or 220 less than the entire object 120 or 220 and a dimension (or diameter) that is at least twice a dimension (or diameter) of a region of interest (ROI) 122 or 222 of the volume. In some embodiments, iterating on the volume of the object 120 or 220, further comprises: storing the volume in memory 430 with a size to store a portion of the object 120 or 220 less than the entire object 120 or 220 and a dimension (or diameter) that has a larger dimension (or diameter) than a region of interest (ROI) 122 or 222 of the volume.

In some embodiments, iterating on the volume of the object 120 or 220, further comprises: partitioning the volume into the non-truncated part 122 or 242 and the at least one truncated part 144 or 244.

In some embodiments, the iterative reconstruction or iterating on the volume of the object 120 or 220 terminates after a predetermined count of iterations or when a measurement on the cost function ($J(\mu)$ or Expression 4) decreases below a specified value or threshold.

In some embodiments, the method further comprises after iterating on the volume of the object 120 or 220: cropping a region of interest (ROI) 122 or 222 of the object 120 or 220 substantially imaged and captured by the non-truncated part of the volume 122 or 242.

In some embodiments, at least one non-transitory machine-readable storage medium comprising a plurality of instructions are adapted to be executed to implement the methods above.

Figure 8:
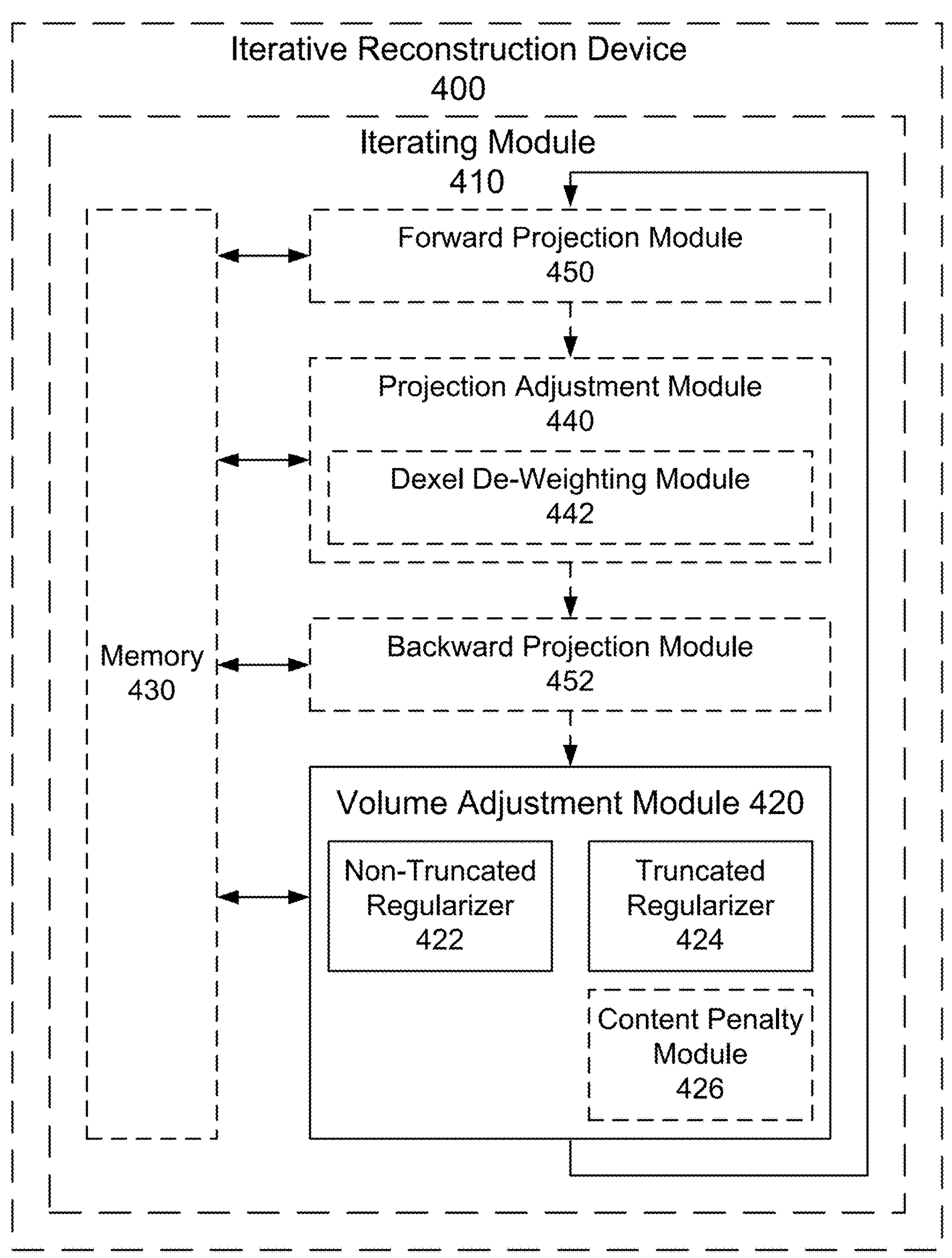
FIG. 8 illustrates a block diagram of an iterative reconstruction device.

FIG. 8 illustrates a block diagram of an iterative reconstruction device 400 comprising: an iterating module 410 configured to iterate on a volume of an object 122 or 242 including a non-truncated part 122 or 242 based on imaged data and at least one truncated part 144 or 244 representing deficiently imaged data, where the volume is represented by voxels. The iterating module 410 further comprises: a volume adjustment module 420 configured to regularize the volume. The volume adjustment module 420 further comprises: a non-truncated regularizer 422 configured to regularize the non-truncated part of the volume 122 or 242 using a standard (or normal) regularization cost function; and a truncated regularizer 424 configured to regularize the truncated part of the volume 144 or 244 using a truncated regularization cost function more aggressive (or greater) than the standard regularization cost function. In an example, the standard regularization cost function $J_S(\mu)$ represented by Expression 5 or Expression 6.

$$J_S(\mu)=F(\mu)+\lambda_N R_N(\mu \qquad \text{[Expression 5]}$$

$$J_S(\mu)=F(\mu)+\lambda_S R_S(\mu) \qquad \text{[Expression 6]}$$

$R_S$ is the standard regularizer and $\lambda_S$ is the standard regularization weight.

In an example, the truncated regularization cost function $J_S(\mu)$ represented by Expression 7 or Expression 8.

$$J_S(\mu)=F(\mu)+\lambda_T R_T(\mu) \qquad \text{[Expression 7]}$$

$$J_S(\mu)=F(\mu)+\lambda_T R_T(\mu)+\lambda_C R_C(\mu) \qquad \text{[Expression 8]}$$

In some embodiments, the volume adjustment module 420 further comprises: a content penalty module 426 configured to apply a content penalty ($R_C$) on the truncated part of the volume 144 or 244.

In some examples, the truncated regularizer uses higher weight than the non-truncated regularizer. In other examples, the non-truncated regularizer includes an edge preserving regularizer; and the truncated regularizer includes a non-edge preserving regularizer.

In some embodiments, the iterating module 410 further comprises: a projection adjustment module 440 configured to adjust the projections of the image data. The projection adjustment module 440 further comprises: a dexel de-weighting module 442 configured to de-weight image data captured by dexels near at least one edge 232 and 234 of the detector 130 or 230. In some examples, the dexel de-weighting module 442 is further configured to use continuous decrement on dexels approaching the edge 232 and 234 of the detector 130 or 230. In other examples, the dexel de-weighting module 442 is further configured to de-weight a fixed border (FB) of dexels on at least one edge 232 and 234 of a detector 130 or 230. In other examples, the dexel de-weighting module 442 is further configured to include reduced weights (RW) for a redundancy region 122 or 224 of the detector 130 or 230.

In some embodiments, the iterative reconstruction device 400 further comprises: a cropping module (or crop module) configured to crop a region of interest (ROI) 122 or 222 of the object 120 or 220 substantially imaged and captured by the non-truncated part of the volume 144 or 244.

In some embodiments, the iterative reconstruction device 400 further comprises: a detector 130 or 230 configured to capture image data, where the dexels near at least one the edge 232 and 234 of the detector 130 or 230 are de-weighted differently from the dexels in the center of the detector 130 or 230.

In some embodiments, the iterative reconstruction device 400 or the volume adjustment module 420 further comprises: memory 430. In an example, the memory 430 can be configured with a size to store the entire object 120 or 220. In another example, the memory 430 can be configured with a size to store a portion of the object 120 or 220 with a dimension (or diameter) that is at least twice a dimension (or diameter) of a region of interest (ROI) 122 or 222 of the volume. The memory 430 may include a variety of circuits. Examples of the memory 430 include a dynamic random access memory (DRAM), a double data rate synchronous dynamic random access memory (DDR SDRAM) according to various standards such as DDR, DDR2, DDR3, DDR4, static random access memory (SRAM), non-volatile memory such as flash memory, spin-transfer torque magentoresistive random access memory (STT-MRAM), Phase-Change RAM, nanofloating gate memory (NFGM), or polymer random access memory (PoRAM), magnetic or optical media, or the like. The memory 430 may be configured to store instructions that, when executed, cause a processor or central processing unit (CPU), a graphics processing unit (GPU), other peripheral devices, or the like to perform the operations described herein.

In some embodiments, the iterative reconstruction device 400 or the iterating module 410 further comprises: a partition module configured to partition the volume into the non-truncated part 122 or 242 and the at least one truncated part 144 or 244.

In some embodiments, the iterating module 410 or the volume adjustment module 420 further comprises: an optimization module configured to optimize the regularization weights between minimizing a fidelity term and minimizing regularization terms, wherein the regularization terms include the normal regularizer (or the first regularizer) 422, the aggressive regularizer (or the second regularizer) 424, and a content penalty.

In some embodiments, the iterating module 410 further comprises: a forward projection module 450 to apply forward projection of the imaged data as described herein. In some embodiments, the iterating module 410 further comprises: a backward projection module 452 to apply backward projection of the imaged data as described herein.

In some embodiments, a system comprises the iterative reconstruction device, as described herein, and at least two of: a scatter correction module; a deblur module; a gain or air correction module; a detector-offsets correction module; a lag correction module; a beam-hardening correction module; and a ring-correction module. The scatter correction module is configured to adjust for object scatter where some of the primary photons (i.e., emitted directly from the X-ray source) that interact with the object are redirected rather than stopped, and some of those redirected photons (i.e., scattered photons or reflected photons) are captured by the detector at a location other than where the primary beam intersects the detector. Such scattered x-rays can cause artifacts such as blurring, shading, or loss of contrast. The scatter correction module can also address scatter from other parts of the scanner, such as from the collimators or from the detector housing. Scatter correction approaches include adaptive kernel based methods (e.g., fASKS), or simulation-based approaches (e.g., Varex's 3D VSHARP correction). The deblurring module (e.g., Varex's REA) is configured to adjust for blur inherent in the detector, most commonly from scintillator light spread (i.e., a scintillator converts high energy x-ray photons into lower energy optical photons that can be detected by a photo-diode), where optical photons could travel several dexels away from the intended dexel before intersecting a photodiode. Deblurring may also account for other blur sources including x-ray scatter, where x-rays that are absorbed into the detector cause secondary electrons or scattered photons that travel several dexels before being absorbed; or electronic crosstalk, where the photodiodes or integrators electrically bleed into their neighbors spatially. A gain, air, or detector-offset correction module is configured to correct respectively for amplifier gains in the detector, spatial variations in the source profile, or electronic offsets or dark currents in the detector. The lag correction module is configured to adjust for a temporal bleed between detector readings, and can model effects such as scintillator afterglow or charge trapping in the detector substrate (e.g., amorphous silicon). The beam hardening correction (BHC) module is configured to adjust for the hardening of spectra (i.e., where disproportionately more low-energy photons are lost than high-energy photons) as the beam passes further through object, and is caused by the fact that in typical CT energies, for any given material, attenuation coefficient generally decreases as a function of energy. BHC makes attenuation look non-linear relative to the theoretical Beer-Lambert equation that much of CT is modeled on, and can result in cupping, shading, or streaking artifacts when not corrected. The ring correction (RC) module is configured to correct for subtle differences in non-linearities in the dexels (e.g., in amplifier performance, scintillator face quality, photo-diode performance, and the like), where for circular scans the contributions of a dexel to backprojection look like a set of tangents to a circle, and hence any anomalous performance of that one dexel will appear as an anomalous circle in the reconstruction. RC performs automated image analysis to automatically remove such circles.

Figure 9:
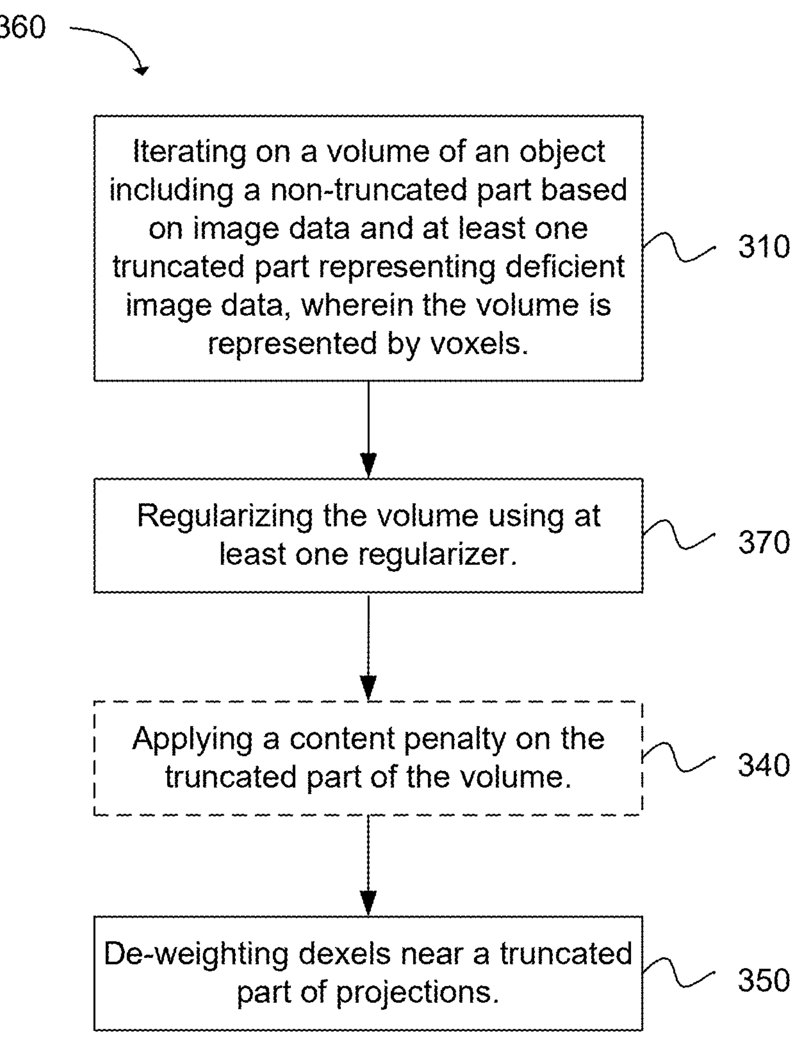
FIG. 9 is a flowchart illustrating an example of a method for handling truncated data in iterative reconstruction.

FIG. 9 illustrates a flowchart of a method for handling truncated data in iterative reconstruction 360. The method for handling truncated data in iterative reconstruction 360 comprises: iterating on a volume of an object 120 or 220 including a non-truncated part 122 or 242 based on image data and at least one truncated part 144 or 244 representing deficiently imaged data, wherein the volume is represented by voxels, as in step 310. The iterating includes: regularizing the volume using at least one regularizer 422 or 424, as in step 370; and de-weighting dexels near a truncated part of projections 154 or 254, as in step 350.

In some embodiments, regularizing the volume using at least one regularizer 422 or 424 further comprises: regularizing the non-truncated part of the volume 122 or 242 using a first regularizer (or non-truncated regularizer) 422, as in step 320 (FIG. 7); and regularizing the truncated part of the volume 144 or 244 using a second regularizer (or truncated regularizer) 424 different from the first regularizer 422, as in step 330 (FIG. 7).

In an example, de-weighting dexels use continuous decrement on dexels approaching the edge 232 and 234 of the detector 130 or 230. In another example, de-weighting dexels de-weight a fixed border (FB) of dexels on at least one edge 232 and 234 of the detector 130 or 230 or includes reduced redundancy weighting (RW) for a redundancy region 122 or 224 of the detector 130 or 230.

In some embodiments, iterating on the volume of the object 120 or 220 further comprises: applying a content penalty ($R_C$) on the truncated part of the volume 144 or 244, as in step 340.

Figure 10:
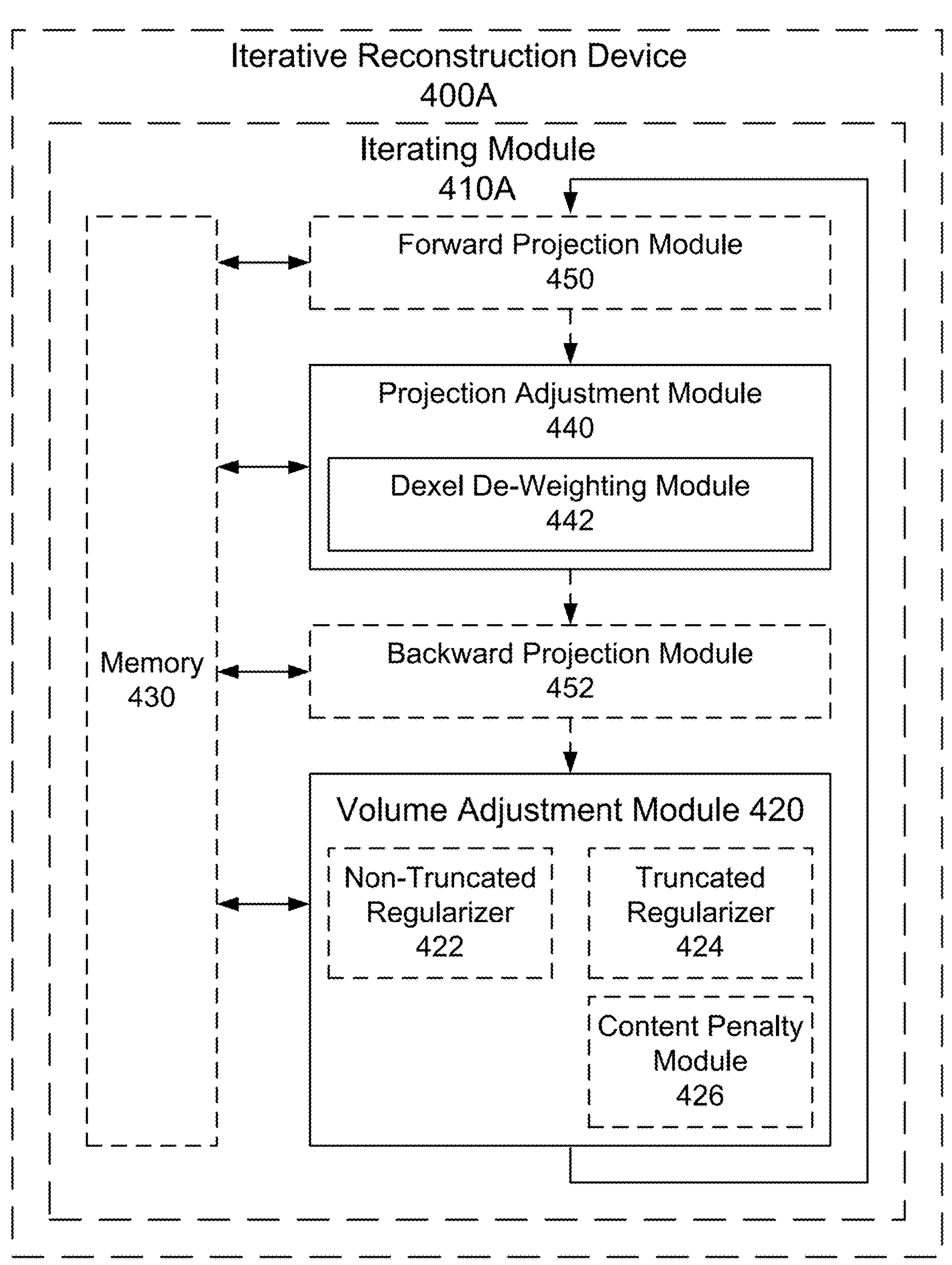
FIG. 10 illustrates a block diagram of an iterative reconstruction device.

FIG. 10 illustrates a block diagram of an iterative reconstruction device 400A comprising: an iterating module 410A configured to iterate on a volume of an object 122 or 242 including a non-truncated part 122 or 242 based on imaged data and at least one truncated part 144 or 244 representing deficiently imaged data, where the volume is represented by voxels. The iterating module 410 further comprises: a volume adjustment module 420 configured to regularize the volume. The volume adjustment module 420 further comprises: at least one regularizer 422 or 424 configured to regularize the non-truncated part of the volume 122 or 242 and the truncated part of the volume 144 or 244; and a projection adjustment module 440 configured to adjust the projections of the image data, wherein the projection adjustment module 440 comprises a dexel de-weighting module 442 configured to de-weight image data captured by dexels near at least one edge 232 and 234 of the detector 130 or 230. In an example, the at least one regularizer includes a spatial regularizer.

In some embodiments, the iterative reconstruction device 400A or the iterating module 410A can include the features and modules as described related to FIG. 8.

Some embodiments include an iterative reconstruction device, comprising: an iterating means for iterating on a volume of an object including a non-truncated part 122 or 242 based on image data and at least one truncated part 144 or 244 representing deficiently imaged data, where the volume is represented by voxels. The iterating means further comprises: a volume adjustment means for regularizing the non-truncated part 122 or 242 of the volume using a standard (or normal) regularization means and regularizing the truncated part of the volume 144 or 244 using an aggressive regularization means with a cost function more aggressive (or greater) than the standard regularization means. Examples of iterating means include the iterating module 410 and other mechanisms that can repeat a function (in a loop) for a predetermined count of iterations or until a measurement on the cost function decreases below a specified value or threshold. Examples of volume adjustment means include the volume adjustment module 420, the standard regularization means, and the aggressive regularization means. Examples of standard regularization means include the non-truncated regularizer 422, the edge preserving regularizer, TV regularizer, and Huber regularizer. Examples of aggressive regularization means include the truncated regularizer 424, the non-edge preserving regularizer, quadratic regularizer, and a regularizer including a content penalty whose value is lower for dexel values closer to zero, and higher for dexel values farther from zero.

In some embodiments, the volume adjustment means further comprises a content penalty means for applying a content penalty on the truncated part of the volume. Examples of weighting means include the content penalty module 426 and other mechanisms that can give greater weight to edge voxels of the truncated part of the volume.

In some embodiments, the iterative reconstruction device further comprises: a de-weighting means for de-weighting dexels near a truncated part of projections; or a cropping means for cropping a region of interest (ROI) of the object substantially imaged and captured by the non-truncated part of the volume. Examples of de-weighting means include the dexel de-weighing module 440, and other mechanisms that can change the weights at a continuous decrement on dexels approaching the edge of the detector or use a fixed border de-weighting of dexels on at least one edge of a detector or reduce weights RW for a redundancy region of the detector. Examples of cropping means include cropping module (or crop module) and other mechanisms that can cropped a larger volume to down to the ROI 122 and 222.

The summary provided above is illustrative and is not intended to be in any way limiting. In addition to the examples described above, further aspects, features, and advantages of the invention will be made apparent by reference to the drawings, the following detailed description, and the appended claims.

Circuitry can include hardware, firmware, program code, executable code, computer instructions, and/or software. A non-transitory computer readable storage medium can be a computer readable storage medium that does not include a signal.

It should be understood that many of the functional units described in this specification have been labeled as modules, in order to more particularly emphasize their implementation independence. For example, a module may be implemented as a hardware circuit comprising custom very-large-scale integration (VLSI) circuits or gate arrays, including but not limited to logic chips, transistors, or other components. A module may also be implemented in programmable hardware devices, including but not limited to field programmable gate arrays (FPGA), programmable array logic, programmable logic devices or similar devices.

Reference throughout this specification to an "example" or an "embodiment" means that a particular feature, structure, or characteristic described in connection with the example is included in at least one embodiment of the invention. Thus, appearances of the words an "example" or an "embodiment" in various places throughout this specification are not necessarily all referring to the same embodiment.

Furthermore, the described features, structures, or characteristics may be combined in a suitable manner in one or more embodiments. In the following description, numerous specific details are provided (e.g., examples of layouts and designs) to provide a thorough understanding of embodiments of the invention. One skilled in the relevant art will recognize, however, that the invention can be practiced without one or more of the specific details, or with other methods, components, layouts, etc. In other instances, well-known structures, components, or operations are not shown or described in detail to avoid obscuring aspects of the invention.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description. These additional embodiments are determined by replacing the dependency of a given dependent claim with the phrase "any of the claims beginning with claim [x] and ending with the claim that immediately precedes this one," where the bracketed term "[x]" is replaced with the number of the most recently recited independent claim. For example, for the first claim set that begins with independent claim 1, claim 4 can depend from either of claims 1 and 3, with these separate dependencies yielding two distinct embodiments; claim 5 can depend from any one of claim 1, 3, or 4, with these separate dependencies yielding three distinct embodiments; claim 6 can depend from any one of claim 1, 3, 4, or 5, with these separate dependencies yielding four distinct embodiments; and so on.

Recitation in the claims of the term "first" with respect to a feature or element does not necessarily imply the existence of a second or additional such feature or element. Elements specifically recited in means-plus-function format, if any, are intended to be construed to cover the corresponding structure, material, or acts described herein and equivalents thereof in accordance with 35 U.S.C. § 112 (f). Embodiments of the invention in which an exclusive property or privilege is claimed are defined as follows.

What is claimed is:

1. A method for handling truncated data in iterative reconstruction, the method comprising:

rotating an imaging source and a detector around an object through a plurality of different projection angles, each projection angle being associated with a corresponding non-truncated part and a truncated part;

generating an image for each of the projection angles;

identifying a non-truncated part of a volume of the object and at least one truncated part of the volume of the object representing deficiently imaged data based on the images and intersections of non-truncated projection regions for all of the projection angles, wherein the volume is represented by voxels where the non-truncated part corresponds to intersections of non-truncated projection regions for all projection angles; and iterating on the volume of the object, wherein iterating includes:

regularizing the non-truncated part of the volume using a first regularizer with a first function of a first type, wherein the first regularizer comprises a total variation regularizer or a Huber regularizer; and regularizing the truncated part of the volume using a second regularizer with a second function of a second type that is different from the first type of the first function of the first regularizer, wherein the second regularizer comprises:

a quadratic spatial regularizer based on a gradient of a reconstruction volume value of a given voxel; and a content penalty for the given voxel based on the reconstruction volume value of the given voxel.

2. The method of claim 1, wherein iterating on the volume of the object further comprises:

de-weighting dexels near a truncated part of projections.

3. The method of claim 1, wherein the first regularizer comprises spatial regularization.

4. The method of claim 1, wherein the second regularizer comprises spatial regularization.

5. The method of claim 1, wherein regularizing the non-truncated part of the volume and regularizing the truncated part of the volume further comprises:

minimizing a sum of a fidelity term and regularization terms, wherein the regularization terms include a first regularization term corresponding to the first regularizer, a second regularization term corresponding to a spatial portion of the second regularizer, and a third regularization term corresponding to the content penalty for the given voxel based on the reconstruction volume value of the given voxel in the second regularization term.

6. The method of claim 1, wherein iterating on the volume of the object further comprises:

storing the volume in memory with a size to store the object.

7. The method of claim 1, wherein iterating on the volume of the object further comprises:

storing the volume in memory with a size to store a portion of the object with a dimension that is at least twice a dimension of a region of interest (ROI) of the volume.

8. The method of claim 1, wherein iterating on the volume of the object terminates after a predetermined count of iterations or when a measurement on a cost function decreases below a specified threshold.

9. The method of claim 1, further comprising after iterating on the volume of the object:

cropping a region of interest (ROI) of the object substantially imaged and captured by the non-truncated part of the volume.

10. At least one non-transitory machine-readable storage medium comprising a plurality of instructions adapted to be executed to implement the method of claim 1.

11. An iterative reconstruction device, comprising:

an imaging source;

a detector disposed relative to the imaging source such that the imaging source and the detector are rotatable around an object through a plurality of different projection angles, each projection angle being associated with a corresponding non-truncated part and a truncated part, wherein the detector is configured to generate an image for each of the projection angles; and a non-transitory computer readable storage medium storing code comprising instructions executable by a processor to:

identify a non-truncated part of a volume of the object and at least one truncated part of the volume of the object representing deficiently imaged data based on the images and intersections of non-truncated projection regions for all of the projection angles, wherein the volume is represented by voxels where the non-truncated part corresponds to intersections of non-truncated projection regions for all projection angles; and iterate on the volume of the object wherein the iterating comprises:

regularizing the volume, the regularizing-comprising applying:

a non-truncated regularizer configured to regularize the non-truncated part of the volume using a standard regularization cost function of a first type, and a truncated regularizer configured to volume smooth the truncated part of the volume using a truncated regularization cost function of a second type that is different from the first type of the standard regularization cost function and is more aggressive than the standard regularization cost function;

wherein the difference between the function of the first type and the function of the second type includes a difference other than a difference in weights; and wherein the truncated regularizer comprises a quadratic spatial regularizer based on a gradient of a reconstruction volume value of a given voxel, and a content penalty for the given voxel that penalizes the reconstruction volume value of the given pixel based on the reconstruction volume value of the given voxel.

12. The iterative reconstruction device of claim 11, wherein:

the truncated regularizer uses higher weight than the non-truncated regularizer; or the non-truncated regularizer includes an edge preserving regularizer, and the truncated regularizer includes a non-edge preserving regularizer.

13. The iterative reconstruction device of claim 11, wherein the iterating further comprises:

adjusting the images, the adjusting-comprising:

de-weighting-image data of the images captured by dexels near at least one edge of the detector.

14. The iterative reconstruction device of claim 13, wherein the de-weighting further comprises:

using continuous decrement on dexels approaching the edge of the detector; or de-weighting a fixed border (FB) of dexels on at least one edge of the detector; or including reduced weights (RW) for a redundancy region of the detector.

15. The iterative reconstruction device of claim 11, wherein the code further comprises instructions executable by the processor to:

crop a region of interest (ROI) of the object substantially imaged and captured by the non-truncated part of the volume.

16. The iterative reconstruction device of claim 11, wherein the code further comprises instructions executable by the processor to:

de-weight dexels near at least one edge of the detector differently from dexels in the center of the detector.

17. A system, comprising the iterative reconstruction device of claim 11 and at least two of:

a scatter correction module;

a deblur module;

a gain or air correction module;

a detector-offsets correction module;

a lag correction module;

a beam-hardening correction module; or a ring-correction module.

18. An iterative reconstruction device, comprising:

an imaging source for generating radiation;

a detector for receiving the radiation, wherein the imaging source and the detector are rotatable together around an object through a plurality of different projection angles, each projection angle being associated with a corresponding non-truncated part and a truncated part, wherein the detector is further for generating an image for each of the projection angles; and a non-transitory computer readable storage medium storing code comprising instructions executable by a processor to:

identify a non-truncated part of a volume of the object and at least one truncated part of the volume of the object representing deficiently imaged data based on the images and intersections of non-truncated projection regions for all of the projection angles, wherein the volume is represented by voxels where the non-truncated part corresponds to intersections of non-truncated projection regions for all projection angles;

iterate on the volume of the object, wherein the iterating comprises:

regularizing the non-truncated part of the volume using a standard regularization with a first regularization cost function of a first type;

regularizing the truncated part of the volume using an aggressive regularization with a second regularization cost function of a second type that is different from and more aggressive than the first type of the first regularization cost function of the standard regularization;

wherein the difference between the first regularization cost function of the first type and the second regularization cost function of the second type includes a difference other than a difference in weights;

de-weighting a fixed border (FB) of dexels on an edge of the detector or including reduced weights (RW) for a redundancy region of the detector;

applying a quadratic spatial penalty to reconstruction volume value of voxels in the truncated part of the volume, wherein the quadratic spatial penalty is based on a gradient of the reconstruction volume values of the voxels; and applying a content penalty to the reconstruction volume values of the voxels in the truncated part of the volume, wherein the content penalty has lower values for voxels with reconstruction volume values closer to zero and greater values for voxels with reconstruction volume values farther from zero.

19. The iterative reconstruction device of claim 18, wherein the code further comprises instructions executable by the processor to:

de-weight image data of the images captured by dexels near at least one edge of the detector; or crop a region of interest (ROI) of the object substantially imaged and captured by the non-truncated part of the volume.

* * * * *